United States Patent
Bornzin et al.

(10) Patent No.: US 11,529,522 B2
(45) Date of Patent: Dec. 20, 2022

(54) SYSTEMS AND METHODS FOR IMPLANTING A MEDICAL DEVICE USING AN ACTIVE GUIDEWIRE

(71) Applicant: Pacesetter, Inc., Sylmar, CA (US)

(72) Inventors: Alexander R. Bornzin, Los Angeles, CA (US); Gene A. Bornzin, Santa Monica, CA (US); Zoltan Somogyi, Simi Valley, CA (US); Wenwen Li, San Jose, CA (US); Xiaoyi Min, Ventura, CA (US)

(73) Assignee: Pacesetter, Inc., Sylmar, CA (US)

( * ) Notice: Subject to any disclaimer, the term of this patent is extended or adjusted under 35 U.S.C. 154(b) by 0 days.

(21) Appl. No.: 17/007,696

(22) Filed: Aug. 31, 2020

(65) Prior Publication Data

US 2022/0062644 A1 Mar. 3, 2022

(51) Int. Cl.
*A61N 1/37* (2006.01)
*A61N 1/05* (2006.01)

(52) U.S. Cl.
CPC ........... *A61N 1/371* (2013.01); *A61N 1/0573* (2013.01)

(58) Field of Classification Search
CPC ...... A61N 1/371; A61N 1/0573; A61N 1/362; A61N 1/3621; A61N 1/37512; A61M 2025/09125; A61M 2025/09175
See application file for complete search history.

(56) References Cited

U.S. PATENT DOCUMENTS

| | | | | |
|---|---|---|---|---|
| 2003/0083727 | A1* | 5/2003 | Casavant | A61N 1/0573 607/122 |
| 2012/0165810 | A1* | 6/2012 | Gillberg | A61N 1/3621 606/41 |
| 2014/0114387 | A1* | 4/2014 | Poore | A61N 1/0573 607/127 |
| 2015/0151116 | A1* | 6/2015 | Ollivier | A61N 1/0573 606/41 |

OTHER PUBLICATIONS

Wilkoff et al. "Dual-Chamber Pacing or Ventricular Backup Pacing in Patients with an Implantable Defibrillator: The Dual Chamber and Wl Implantable Defibrillator (DAVID) Trial)" American Medical Association; vol. 288, No. 24; Dec. 2002 (9 pages).
Lamas et al. "Ventricular Pacing or Dual-Chamber Pacing For Sinus-Node Dysfunction" The New England Journal of Medicine; vol. 346, No. 24; Jun. 2002 (9 pages).

* cited by examiner

*Primary Examiner* — Carl H Layno
*Assistant Examiner* — Anh-Khoa N Dinh
(74) *Attorney, Agent, or Firm* — The Small Patent Law Group LLC; Dean D. Small

(57) ABSTRACT

Systems and methods for implanting a lead. The system includes an active guidewire having proximal and distal ends. The distal end includes a guidewire anchor that is configured to be attached to a target SOI. The active guidewire is configured to be utilized to electrically map the target SOI by at least one of delivering stimulation energy through the active guide wire to the target SOI or sensing an evoked response at the target SOI from the guidewire. The (Continued)

system also includes a lead having a lead body with proximal and distal ends and with a lumen extending between the proximal and distal ends. The distal end of the lead body is configured to receive the proximal end of the active guidewire. The lumen is configured to permit the lead body to be advanced over the active guidewire.

20 Claims, 13 Drawing Sheets

SYSTEMS AND METHODS FOR IMPLANTING A MEDICAL DEVICE USING AN ACTIVE GUIDEWIRE

BACKGROUND

Embodiments of the present disclosure relate generally to systems and methods for implanting medical devices within a patient, and more particularly to delivery systems for implanting one or more leads.

Cardiac pacemakers and implantable cardioverter-defibrillators (ICD) use insulated wires (called leads) to monitor the heart and to also deliver electrical signals or shocks. Various techniques exist for implanting cardiac pacemakers, ICDs, and other medical devices, and each technique may use a set of tools designed for that technique. To position a lead, for example, a number of elongated tools (e.g., needles, guidewires, sheaths, and stylets) are inserted into the body. In many cases, the lead is inserted through the lumen of a catheter (or introducer sheath). After the lead is positioned relative to the heart, the catheter is removed.

Removing the catheter without inadvertently displacing the lead can be challenging. The leads are thin and, when finally positioned, may have a number of bends or twists along its path. Furthermore, the proximal end of the lead includes a connector that is larger than the diameter of the sheath's lumen. To address this issue, splittable or peelable sheaths are used. The sheaths are split and separated from each other as the sheaths are withdrawn from the body. As such, the sheaths may be removed while avoiding the connector at the proximal end of the lead.

Although these splittable/peelable sheaths are useful, the withdrawal process can still be challenging, especially for certain procedures. More recently, the His-Purkinje system has been proposed as a physiologic substitute for right-ventricle pacing. Recent clinical trials demonstrated an increased risk of hospitalization for heart failure (HF) in patients having a high burden of right-ventricle (RV) pacing and consequently an increased risk of arrhythmias. His-bundle pacing (HBP) uses native conduction pathways and could prevent the negative effects of RV pacing and promote ventricular synchrony.

It remains challenging, however, to locate the His bundle and achieve true selective capture. During this procedure, a splittable catheter with a dilator is advanced over a guide wire until the dilator end reaches the atrium or right ventricle. With the catheter in place, the implanter removes the guidewire and the dilator and advances a pacing lead through the lumen of the catheter. In some cases, the pacing lead accepts a stylet to provide rigidity and push-ability to the lead. After the pacing lead is positioned, the catheter is slit and removed, leaving the lead in place.

As discussed above, the implanter is careful when withdrawing the catheter so that the catheter does not strike the connector at the proximal end and dislodge the lead from its desired position. If the lead is dislodged, the lead-implantation procedure must begin again. Repeating the process increases the risk of infection in addition to other complications that may arise during such medical procedures.

SUMMARY

In accordance with embodiments herein, a system is provided. The system includes an active guidewire having proximal and distal ends. The distal end is configured to be located proximate to a target site of interest (SOI) within or proximate to a chamber of the heart. The distal end includes a guidewire anchor that is configured to be attached to the target SOI. The active guidewire is configured to be utilized to electrically map the target SOI by at least one of delivering stimulation energy through the active guide wire to the target SOI or sensing an evoked response at the target SOI from the guidewire. The system also includes a lead having a lead body with proximal and distal ends and with a lumen extending along the body between the proximal and distal ends. The distal end of the lead body is configured to receive the proximal end of the active guidewire. The lumen is configured to permit the lead body to be advanced over the active guidewire until the distal end of the lead body is proximate the target SOI.

In some aspects, the system also includes an external programmer device that can configured to be electrically coupled to the proximal end of the active guidewire. The external programmer device may be configured to electrically map the target SOI.

In some aspects, the target SOI may represent a HIS. The guidewire anchor may be configured to attach the distal end of the active guidewire into a wall of the heart proximate the HIS. The external programmer device may be configured to deliver a HIS paced event as the stimulation energy and to sense the evoked response to determine whether HIS capture was achieved based on the His paced event.

In some aspects, the target SOI may represent a left bundle branch. The guidewire anchor can be configured to attach the distal end of the active guidewire a predetermined depth into a septa wall that separates the right and left ventricles. The external programmer device can be configured to deliver the stimulation energy through the distal end of the active guidewire to the left bundle branch.

In some aspects, the target SOI may represent a pacing site. The external programmer device may be configured to deliver a pacing pulse, as the stimulation energy, through the guidewire to the target SOI and sense the evoked response at a sensing site within or proximate the heart separate from the pacing site.

In some aspects, the target SOI may represent a sensing site. The external programmer device may be configured to sense the evoked response at the sensing site following delivery of a pacing pulse at a pacing site within or proximate the heart separate from the sensing site.

In some aspects, the system also includes a catheter configured to be advanced to or proximate the chamber of the heart having the target SOI. The catheter may have a lumen with a size dimensioned to receive the active guidewire. The size of the lumen in the catheter may be smaller than an outer dimension of the lead body, such that the lead does not fit through the lumen of the catheter.

In some aspects, the catheter may include at least one electrode positioned proximate to a distal end of the catheter. The at least one electrode may be configured to at least one of deliver stimulation energy to the target SOI or sense an evoked response at the target SOI.

In some aspects, the lead includes a lead anchor coupled to the distal end of the lead body. The lead anchor defines an anchor passage that is aligned with the lumen of the lead body. The anchor passage is sized to permit the lead anchor to slide over the active guidewire as the lumen is advanced over the active guidewire.

In some aspects, the lead anchor includes a helical screw that wraps about the anchor passage.

In accordance with embodiments herein, a method of implanting a lead is provided. The method includes advancing an active guidewire to a target site of interest (SOI) within or proximate to a chamber of the heart. The method also includes electrically mapping the target SOI utilizing the active guidewire by at least one of delivering stimulation energy through the active guide wire to the target SOI or sensing an evoked response at the target SOI from the guidewire. The method also includes fixating a distal end of the active guidewire at the target SOI. The method also includes advancing a lead over the active guidewire until a distal end of the lead is located proximate the target SOI.

In some aspects, the fixating the distal end of the active guidewire is performed before the electrically mapping the target SOI utilizing the active guidewire.

In some aspects, the target SOI may represent a His bundle region. Fixating the distal end may include attaching the distal end of the active guidewire into a wall of the heart proximate the His bundle region. Electrically mapping may include delivering a His paced event as the stimulation energy. The method may also include assessing whether capture of the His bundle region was achieved based on the His paced event.

In some aspects, the target SOI represents a left bundle branch. Fixating the distal end may include submerging the distal end of the active guidewire a predetermined depth into a septa wall separating the right and left ventricles. Electrically mapping may include delivering the stimulation energy through the distal end of the active guidewire to the left bundle branch.

In some aspects, the target SOI may represent a pacing site. The electrical mapping may include delivering a pacing pulse, as the stimulation energy, through the guidewire to the target SOI and sensing the evoked response at a sensing site within or proximate the heart separate from the pacing site.

In some aspects, the target SOI may represent a sensing site. Electrical mapping may include sensing the evoked response at the sensing site following delivery of a pacing pulse at a pacing site within or proximate the heart separate from the sensing site.

In some aspects, the method also includes, prior to advancing the active guidewire, advancing a J-tip guidewire, obturator, and catheter to or proximate the chamber of the heart having the target SOI. Prior to advancing the active guidewire, the method may include withdrawing the obturator and J-tip guidewire. The method also includes inserting the active guidewire through the catheter to the target SOI and withdrawing the catheter before advancing the lead over the active guidewire.

In some aspects, advancing the active guidewire may include advancing the active guidewire through the right atrium and through the right ventricle, forcing the distal end of the active guidewire through a septa wall separating the right and left ventricles, advancing the distal end of the active guidewire through the left ventricle and submerging the distal end of the active guidewire into a wall of the left ventricle proximate the Purkinje fiber.

In some aspects, the target SOI may represent at least one of an atrial pacing site, a His bundle pacing site, a left bundle branch pacing site, a right bundle branch pacing site, and LV wall pacing site proximate the LV Purkinje fibers.

In some aspects, the method may also include fixating a distal end of the lead to tissue at the target SOI and removing the guidewire by withdrawing the active guidewire along a lumen within the lead.

DETAILED DESCRIPTION

Figure 1:
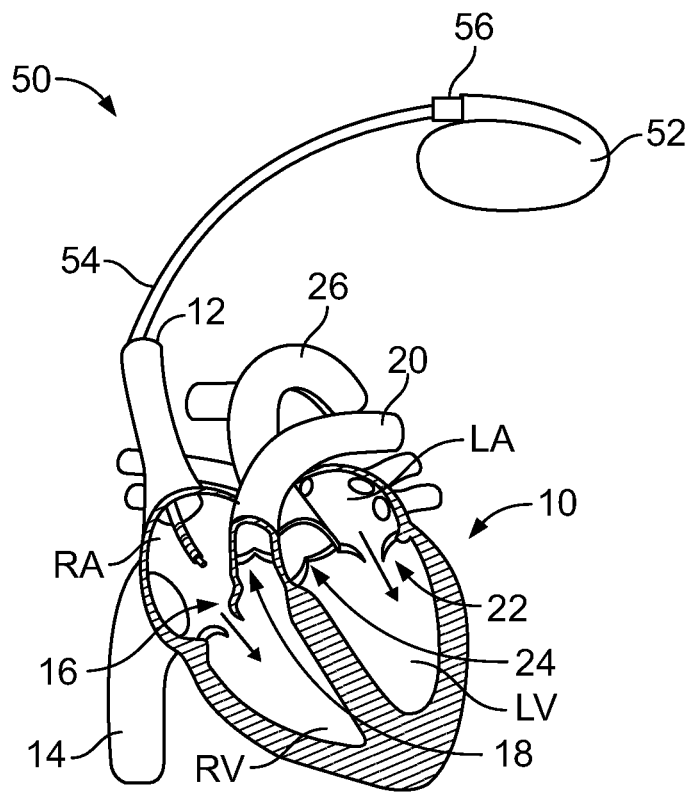
FIG. 1 is a schematic view of a heart illustrated in relation to an implantable medical device (IMD) formed in accordance with an embodiment that includes an implantable lead and a pulse generator interconnected by a lead adaptor.

Embodiments set forth herein include systems for implanting implantable medical devices (IMDs), assemblies or kits of the systems or IMDs, and methods for making and using the same. Particular embodiments use an active guidewire and are implemented in connection with a His-bundle pacing (HBP) strategy or system in which a region of cardiac tissue at or near the His bundle, which is referred to herein as the His bundle region, is stimulated. Although embodiments may be described in relation to HBP, it should be understood that embodiments may be used in connection with a variety of IMDs and medical procedures delivering or using the IMDs. Such procedures may include implanting or extracting leads.

An IMD is a medical device which is intended to be totally or partially introduced into a body (human or animal) and remain in the human body after the procedure. An IMD may include a single component or a system of components that interact to achieve a desired performance. IMDs typically include at least one active component that perform monitoring and/or therapy functions through electrical energy. Non-limiting examples of IMDs include a cardiac monitoring device, a pacemaker, cardioverter, cardiac rhythm management device, defibrillator, neurostimulator, and the like. Many IMDs may provide multiple functions and include implantable cardioverter defibrillators (ICDs) and implantable cardiac resynchronization therapy/defibrillator devices (CRT-Ds).

IMDs often include a control device (e.g., pulse generator) and one or more other components that coordinate with the control device. For example, cardiac IMDs often include a pulse generator and one or more leads. The pulse generator has a power source and electronic circuitry that is configured to monitor the heart. The pulse generator may include one or more processors that implement programmed instructions (e.g., software or firmware) stored in memory of the pulse generator. For example, the pulse generator may be programmed to provide output stimuli (e.g., signals for pacing or a shock) through the lead or leads.

A lead includes one or more insulated electrical conductors that are intended to transfer electrical energy along a length of the lead. For example, the lead may transfer output stimuli from the pulse generator or transmit depolarization potentials from cardiac tissue to a sensing circuit of the pulse generator. A lead typically includes a lead body having an elongated flexible tube or sleeve comprising, for example, a biocompatible material (e.g., polyurethane, silicone, etc.). The lead (or lead body) has a distal end and a proximal end. As used herein, the terms "proximal" and "distal," when used in reference to a lead (or other elongated instruments, such as an introducer sheath, catheter, guidewire, or stylet) are to be understood in relation to delivering and implanting a medical device. During an implantation procedure, "proximal" is to be understood as relatively close to the implanter and "distal" is to be understood as relatively far away from the implanter. After the implantation, a proximal end of a lead is coupled to a pulse generator, and a distal end of the lead is positioned adjacent to tissue (e.g., cardiac or nerve tissue).

The lead body may include a single lumen (or passage) or multiple lumen (or passages) within the flexible tube. A lead may have multiple electrical conductors (not shown) that electrically couple electrode(s) of the lead to the pulse generator. The electrical conductors may be cabled conductors coated with PTFE (poly-tetrafluoroethylene) and/or ETFE (ethylenetetrafluoroethylene). The electrical conductors are terminated to the respective electrode. The lead body may be configured for receiving a guide wire or stylet that enable positioning of the lead.

The lead may include one or more electrodes or one or more contacts through which electrical energy may leave or enter the conductors of the lead. Electrodes may be positioned adjacent to tissue for monitoring or providing therapy thereto. The lead connector also includes one or more contacts that are communicatively coupled to the one or more electrodes. The lead adaptor and the pulse generator are also described as including contacts. To more readily distinguish electrodes and contacts, the electrodes can be described as being positioned at the distal end and the contacts can be described as being positioned at the proximal end of the lead or as part of a lead adaptor or a pulse generator.

Various types of electrodes and contacts exist, including tip electrodes or contacts, ring electrodes or contacts, contact pads, patch electrodes, spring electrodes, or porous electrodes. Electrodes and contacts may also have a variety of configurations or patterns (e.g., unipolar, bipolar or multipolar, array, etc.). In particular embodiments, the electrodes/contacts may be arranged according to international standard 1 (IS-1) that are used for low-voltage applications. The configuration may be unipolar or bipolar. A largest dimension of an IS-1 lead connector is 3.2 mm.

The lead adaptor enables an electrical and mechanical connection between the lead connector and the pulse generator. The lead adaptor may be used to upsize or downsize the lead connector in order to mate with the pulse generator. Optionally, the lead adaptor may also function as a lead extender that effectively increases the length of the lead.

Leads also include a lead connector positioned at the proximal end. The lead connector provides an electrical connection between the one or more electrodes of the lead and the one or more contacts of a control device (e.g., pulse generator). As described herein, the lead connector can also mate with a lead adaptor. The lead adaptor may then mate with the pulse generator to electrically connect the electrodes to the pulse generator and mechanically connect the lead to the pulse generator.

A lead may be delivered and positioned relative to tissue using a catheter (or introducer sheath). A catheter is a tube or cannula that is introduced into the body (e.g., through the vascular system, for example), typically over another elongated instrument, such as a needle, dilator, or guidewire. The catheter includes a lumen that permits passage of other elongated instruments, such as the lead. The catheter may form part of a delivery system (or kit) that includes one or more other elongated instruments, such as a needle, a guidewire, a syringe, a dilator, and one or more other sheaths.

In particular embodiments, the catheter is non-splittable or non-peelable. In such embodiments, the catheter may be removed while the active guidewire is secured to a target SOI. With the catheter removed, an implantable lead may be guided to the target SOI using the active guidewire. In addition to using non-splittable or non-peelable catheters, particular embodiments may enable catheters having a smaller-sized lumen as it is not necessary for the lumen to accommodate the implantable lead.

FIG. 1 illustrates a schematic cutaway view of a heart 10 relative to an IMD 50. The heart 10 includes a right atrium RA, a right ventricle RV, a left atrium LA, and a left ventricle LV. During normal operation of the heart 10, deoxygenated blood from the body is returned to the right atrium RA from the superior vena cava 12 and inferior vena cava 14. The right atrium RA pumps the blood through the atrioventricular or tricuspid valve 16 to the right ventricle RV, which then pumps the blood through the pulmonary valve 18 and the pulmonary artery 20 to the lungs for reoxygenation and removal of carbon dioxide. The newly oxygenated blood from the lungs is transported to the left atrium LA, which pumps the blood through the mitral valve 22 to the left ventricle LV. The left ventricle LV pumps the blood through the aortic valve 24 and the aorta 26 throughout the body.

Figure 2:
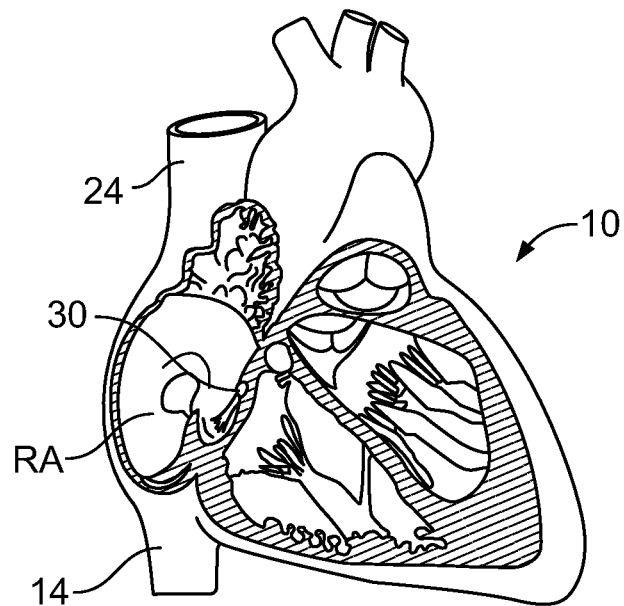
FIG. 2 is another schematic view of the heart showing a location of the His bundle relative to other cardiac structures.

FIG. 2 is another schematic cutaway view of the heart 10 showing a location of the bundle of His 30 in the heart. The bundle 30 consists of fast-conducting muscle fibers that begin at the atrioventricular node in the right atrium and pass to the interventricular septum. The bundle 30 divides in the septum into a right branch that travels along the right side of the septum and supplies excitation to the right ventricle, and a pair of left branches that travel along the left side of the septum and supply excitation to the left ventricle. The fibers in the branches terminate in an extensive network of Purkinje fibers which distribute excitation pulses to the layer of cells beneath the endocardium.

Returning to FIG. 1, the IMD 50 includes a pulse generator 52 that is operably coupled to an implantable lead 54 through a lead adaptor 56. The lead adaptor 56 is configured to receive a lead connector (not shown) of the lead 54. Although the IMD 50 includes only one lead in FIG. 1, a number of other leads (e.g., two, three, four, etc.) may be used. The lead 54 is designed to penetrate the endocardium in contact with His bundle 30. The lead 54 may enter the vascular system through one of several possible vascular access sites and extends through the superior vena cava 12 to the right atrium RA.

In FIG. 1, the IMD 50 is a cardiac pacemaker. In other embodiments, however, the IMD 50 may include an ICD, a CRT-D, an ICD coupled with a pacemaker, and the like. The IMD 50 may be a dual-chamber stimulation device capable of treating both fast and slow arrhythmias with stimulation therapy, including cardioversion, defibrillation, and pacing stimulation, as well as capable of detecting heart failure, evaluating its severity, tracking the progression thereof, and controlling the delivery of therapy and warnings in response thereto. The IMD 50 may be controlled to sense atrial and ventricular waveforms of interest, discriminate between two or more ventricular waveforms of interest, deliver stimulus pulses or shocks, and inhibit application of a stimulation pulse to a heart based on the discrimination between the waveforms of interest and the like.

Although not shown, the IMD 50 may wirelessly communicate with an external device. For example, the external device may initiate the pulse generator 52. The external device and the pulse generator may communicate identification data (e.g., obtain model and serial number) between one another. The external device may generate a chart that correlates to the patient having the pulse generator 52. The external device may instruct the pulse generator 52 to perform an electrode integrity check and measure parameters of the electrodes (e.g., impedance of shock electrode(s)). The external device and/or the pulse generator may determine a sensing configuration for the pulse generator based on cardiac activity. During initiation of the pulse generator 52, therapy parameters may be selected by the user of the external device.

Figure 3:
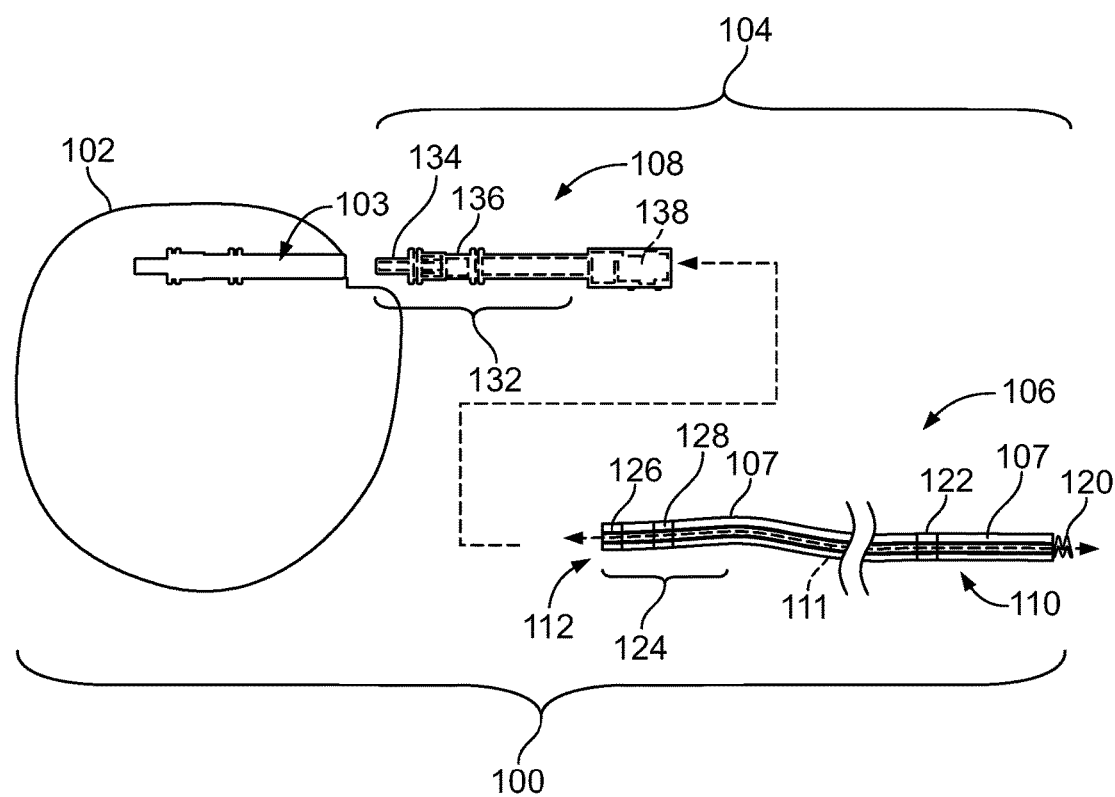
FIG. 3 is a schematic diagram of an IMD formed in accordance with an embodiment that includes an implantable lead, a lead adaptor, and a pulse generator.

FIG. 3 is a schematic diagram of a system 100, which is hereinafter referred to as an implantable medical device (IMD) 100. The IMD 100 is not assembled in FIG. 3. In some embodiments, the IMD 100 may be grouped or packaged as a set or kit. The IMD 100 includes an implantable pulse generator 102 and a lead assembly 104. The pulse generator 102 has a connector cavity 103 that is configured to mate with the lead assembly 104. The lead assembly 104 includes an implantable lead 106 and a lead adaptor 108. The lead 106 includes a lead body 107 that extends lengthwise along a longitudinal axis 111 between a distal end 110 and a proximal end 112. The term longitudinal axis encompasses both linear and non-linear axes. For example, the longitudinal axis 111 may extend along a curved path that changes as the lead body 107 is flexed, bent, twisted, or otherwise manipulated.

The lead body 107 includes a lumen 115 extending along the lead body 107 between the proximal and distal ends 112, 110. The longitudinal axis 111 may extend through a geometric center of the lead body 107. The distal end 110 of the lead body 107 is configured to receive a proximal end (not shown) of an active guidewire, such as the active guidewire 150 (shown in FIG. 5). The lumen 115 is configured to permit the lead body 107 to be advanced over the active guidewire until the distal end 110 of the lead body 107 is proximate a target SOI.

The lead 106 may include a plurality of electrodes 120, 122 positioned at the distal end 110. The electrodes 120, 122 are arranged in a bipolar configuration but other configurations may be used. The lead 106 also has a lead connector 124 positioned at the proximal end 112. The lead connector 124 includes a portion of the lead body 107 and lead contacts 126, 128 that are communicatively coupled to the electrodes 120, 122 through a plurality of conductors (not shown) that are contained within the lead body 107. In the illustrated embodiment, the lead body 107 is iso-diametric such that a diameter of the lead 106 is essentially uniform throughout. The iso-diametric body 107 may permit a catheter (not shown) to slide over the lead connector 124 when the catheter is removed.

Various combinations of the electrodes and contacts may be used in connection with sensing cardiac signals and/or delivering stimulation therapies. For example, the electrodes 120, 122 include a tip electrode 120 and a ring electrode 122, and the lead contacts 126, 128 include a tip contact 126 and a ring contact 128. In other embodiments, however, the electrodes and contacts may include any number of electrodes/contacts and have a variety of types or shapes.

As described herein, the lead body 107 may have a body outer envelope that is configured to fit within a lumen of a catheter and the lead connector 124 has a connector outer envelope configured to fit within the lumen of the catheter. The lead body 107 includes an insulating sheath or housing of a suitable insulative, biocompatible, biostable material such as, for example, silicone rubber or polyurethane, extending substantially the entire length of the lead body and surrounding the conductors.

The lead adaptor 108 is configured to interconnect the implantable lead 106 and the pulse generator 102. As shown, the lead adaptor 108 has an insertable connector 132 that includes mating contacts 134, 136. The lead adaptor 108 also includes and an adaptor cavity 138 that includes cavity contacts. The cavity contacts are positioned to engage the lead contacts 126, 128 of the lead connector 124 when the lead connector 124 is inserted into the adaptor cavity 138 of the lead adaptor 108. The insertable connector 132 is configured to be inserted into the connector cavity 103 of the pulse generator 102.

Figure 4:
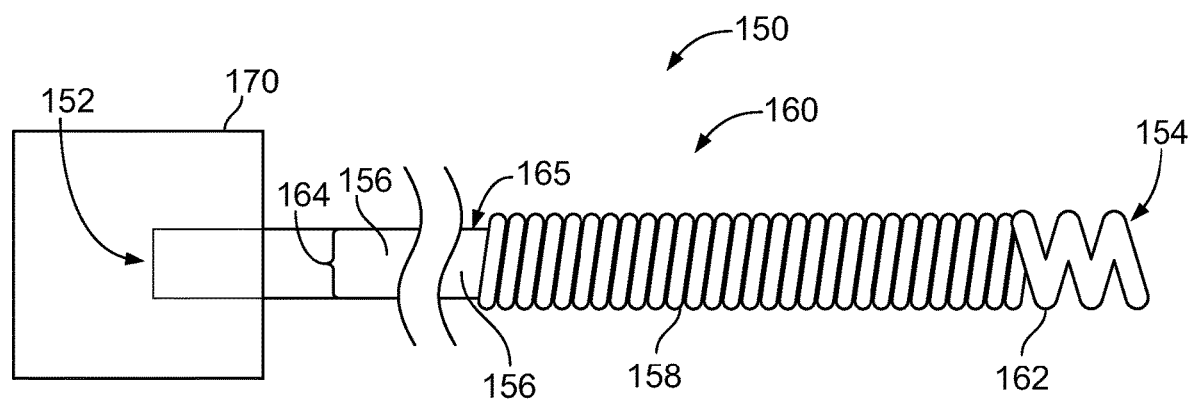
FIG. 4 is a side schematic view of an active guidewire formed in accordance with an embodiment.

FIG. 4 is a schematic side view of an active guidewire 150 formed in accordance with an embodiment. The active guidewire 150 includes a proximal end 152 and a distal end 154 and a wire body (or core) 156 that extends between the proximal and distal ends 152, 154. The wire body 156 may comprise, for example, stainless steel, nickel-titanium alloy (Nitinol), or the like.

The active guidewire 150 is configured to be communicatively coupled to an external programmer device 170. The external programmer device is configured to electrically map the target SOI. To this end, the external programmer device 170 includes one or more processors and memory that stores program instructions directing the processors to perform electrical mapping operations. For example, one or more processors of the device may control the external programmer device 170 to deliver stimulation energy through the active guide wire to the target SOI. One or more processors of the device may control the external programmer device 170 to sense an evoked response at the target SOI from the active guidewire.

The external programmer device 170 is configured to locate a target site of interest (SOI) of tissue, such as a target SOI within or proximate to a chamber of the heart. The target SOI may be a pacing site or a sensing site. The target SOI may represent at least one of an atrial pacing site, a HIS pacing site, a left bundle branch pacing site, a right bundle branch pacing site, and LV wall pacing site proximate the LV Purkinje fibers.

The proximal end 152 of the active guidewire 150 may be directly or indirectly coupled to the external programmer device 170 as shown in FIG. 4. In some embodiments, the proximal end 152 may be directly coupled to a terminal of the external programmer device 170. Alternatively, the proximal end 152 may be directly coupled to a transmitter that communicates with the external programmer device 170. The external programmer device 170 may receive mapping data in the form of electrical signals that are transmitted through the active guidewire 150.

The active guidewire 150 may include a coil 158 that is wrapped about the wire body 156. As shown in FIG. 5, the coil 158 is wrapped about a distal segment 160 of the active guidewire 150 that includes the distal end 154. In particular embodiments, the distal segment 160 of the active guidewire 150 has a designated shape.

The active guidewire 150 also includes a fixation anchor 162. In the illustrated embodiment, the fixation anchor 162 is shaped such that, when directed toward the target SOI and rotated about a central axis, the fixation anchor 162 is driven into the tissue, thereby affixing the distal end 154 to the tissue. The designated shape of the distal segment 160 may decrease the likelihood that the fixation anchor 162 inadvertently engages or snags other tissue while the active guidewire 150 is advanced through the body. For example, the distal segment 160 may yield a J-shaped tip when the distal segment 160 is in an unbiased state.

In some embodiments, the active guidewire 150 has an average operating diameter 164 that is between 0.040" and 0.025". The average working diameter is a diameter of the active guidewire that is inserted into the body or, more particularly, inserted into the heart. In certain embodiments, the active guidewire 150 has an average operating diameter 164 that is between 0.036" and 0.028" or, more particularly, between 0.034" and 0.030".

The coil 158 and/or the fixation anchor 162 may have a cross-sectional shape that is circular, oval-like, or ribbon-like. The coil 158 and/or the fixation anchor 162 may comprise discrete elements or may be shaped from the same piece of material. For example, a wire that defines the coil 158 and/or the fixation anchor 162 may comprise a stiff metal having a high shear modulus. For example, the wire may include platinum, platinum iridium alloy, 304 stainless steel, 316 stainless steel, 316L stainless steel, or the like. The wire may have an outer diameter that is between 0.003" and less than 0.011" or, more specifically, between 0.004" and less than 0.010". In particular embodiments, the wire has an outer diameter that is between 0.005" and less than 0.009".

Optionally, the active guidewire 150 may include one or more coatings 165. For example, the one or more coatings 165 may include an electrically-insulative coating, such as parylene, PTFE, ethylene tetrafluoroethylene (ETFE), or the like. Optionally, the one or more coatings 165 may include a hydrophobic or hydrophilic coating along a portion or an entirety of the wire to reduce the friction between the guidewire 150 and the lead. A lumen of the lead may include an inner surface comprising polytetrafluoroethylene, ETFE, or the like. For example, the lumen may be defined by a cylindrical core comprising polytetrafluoroethylene, ETFE, or the like. In some embodiments, the lead is similar or identical to one or more embodiments described in U.S. Pat. No. 9,623,235, which is hereby incorporated by reference in its entirety.

The fixation anchor 162 is electrically active such that fixation anchor may function as an electrode. For example, the fixation anchor 162 may form part of a conductive pathway that is configured for at least one of pacing or sensing electrical activity of the tissue. The fixation anchor 162 may also be used for mapping. By way of example, a length of the fixation anchor 162 may be at least 1.0 mm. In some embodiments, the fixation anchor 162 has a length that enables a deeper penetration into tissue. In particular embodiments, the fixation anchor 162 has a length between 2.0 mm and 5.0 mm that is configured to reach into septal tissue to achieve left or right bundle branch block correction. Optionally, when the fixation anchor 162 is greater than 2.00 mm a portion of the fixation anchor may be coated with parylene so that the proximity of the target tissue may be more precisely identified.

The fixation anchor 162 may be configured to sense electrical activity to identify the target SOI. Sensing with the fixation anchor 162 may be achieved in a unipolar mode while sensing between fixation anchor 162 and a remote electrode (not shown). The remote electrode may be, for example, a surgical clamp positioned at the pocket or incision.

Alternatively, a local electrogram may be obtained by using one or more electrodes positioned at a distal end of a catheter. For example, the distal end may include a pair of electrodes. If the electrode pair detects the designated site of tissue, it may not be necessary to use both the electrode pair and the fixation anchor 162 for mapping. Under some circumstances, it may be uncertain whether the His potential is from the electrode pair 104 or the guidewire fixation screw 112.

For some implementations, the target SOI may represent a left bundle branch (LBB). The fixation anchor 162 may be configured (e.g., sized, shaped, and oriented) to attach the distal end 154 of the active guidewire 150 to the target SOI. The fixation anchor 162 may enable achieving a predetermined depth into a septa wall that separates the right and left ventricles. In such embodiments, the external programmer device 170 may deliver stimulation energy through the distal end 154 of the active guidewire 150 to the LBB.

For other implementations, the target SOI represents a pacing site and the external programmer device 170 is configured to deliver a pacing pulse, as the stimulation energy, through the guidewire 150 to the target SOI. The external programmer device 170 may sense the evoked response at a sensing site within or proximate the heart in which the sensing site is separate from the pacing site.

Yet in other implementations, the target SOI represents a sensing site and the external programmer device is configured to sense the evoked response at the sensing site following delivery of a pacing pulse at a pacing site within or proximate the heart that is separate from the sensing site.

Figure 5A:
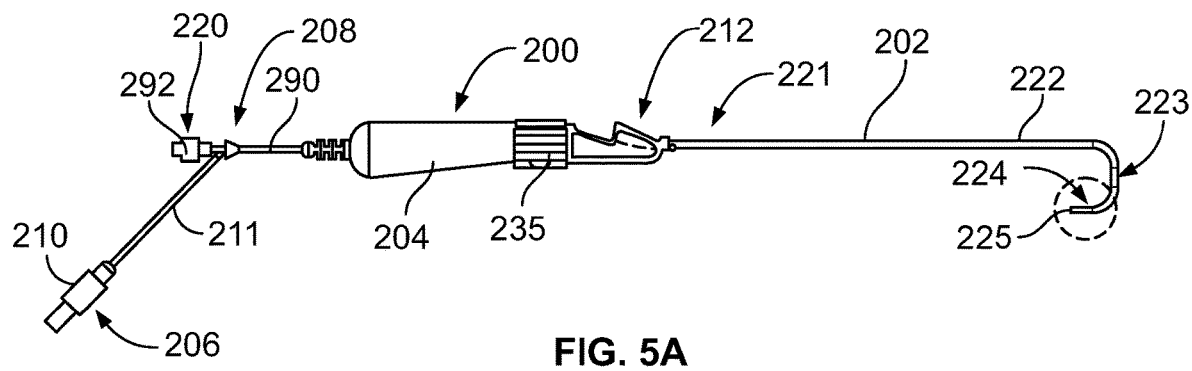
FIG. 5A is a side view of a delivery system formed in accordance with an embodiment that may be used with the active guidewire of FIG. 4.

FIG. 5A is a side view of a delivery system 200 formed in accordance with an embodiment. The delivery system 200 includes a catheter (or introducer sheath) 202, a handle 204, a connector assembly 206, and a fluid flushing assembly 208. Each of these components may be similar or identical to components described in greater detail in U.S. application Ser. No. 16/452,223, filed on Jun. 25, 2019, and U.S. application Ser. No. 16/907,515, filed on Jun. 22, 2020, each of which is incorporated herein by reference in its entirety.

Figure 5B:
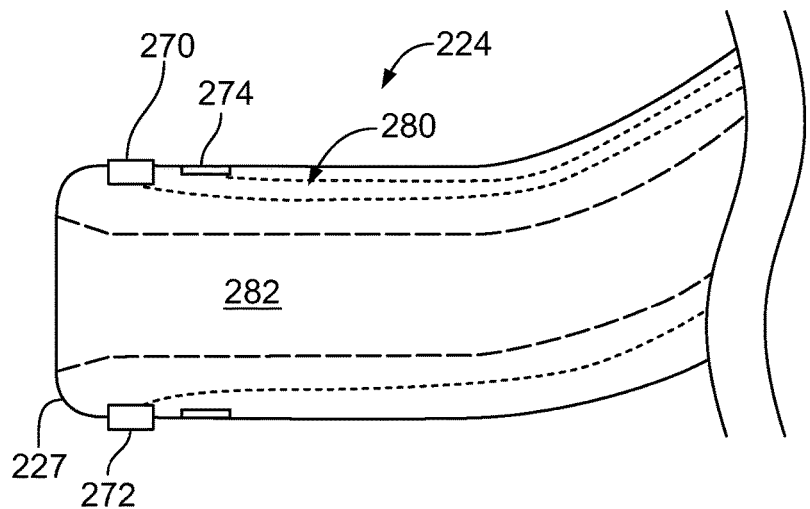
FIG. 5B is an enlarged cross-sectional view of a distal end of a catheter of the delivery system shown in FIG. 5A having a lumen that is configured to allow the active guidewire of FIG. 4 to pass therethrough.

The connector assembly 206 includes an electrical connector 210 coupled to a trailing end of handle 204. The electrical connector 210 is electrically coupled to one or more electrodes along the catheter 202. For example, FIG. 5B is an enlarged cross-sectional view of a distal segment 224 of the catheter 202 as identified by the dashed circle in FIG. 5A. In the illustrated embodiment, the electrical connector 210 (FIG. 5A) is communicatively coupled to electrodes 270, 272 (FIG. 5B) and optionally an electrode 274 (FIG. 5B) through conductors 280 that are embedded within the catheter 202. The electrodes 270, 274 are proximate to a distal tip (or end) 227 of the catheter 202. In particular embodiments, the electrodes 270, 272 are split-ring electrodes. The connector assembly 206 is configured to communicatively couple to an electrogram mapping system (not shown).

Figure 7:
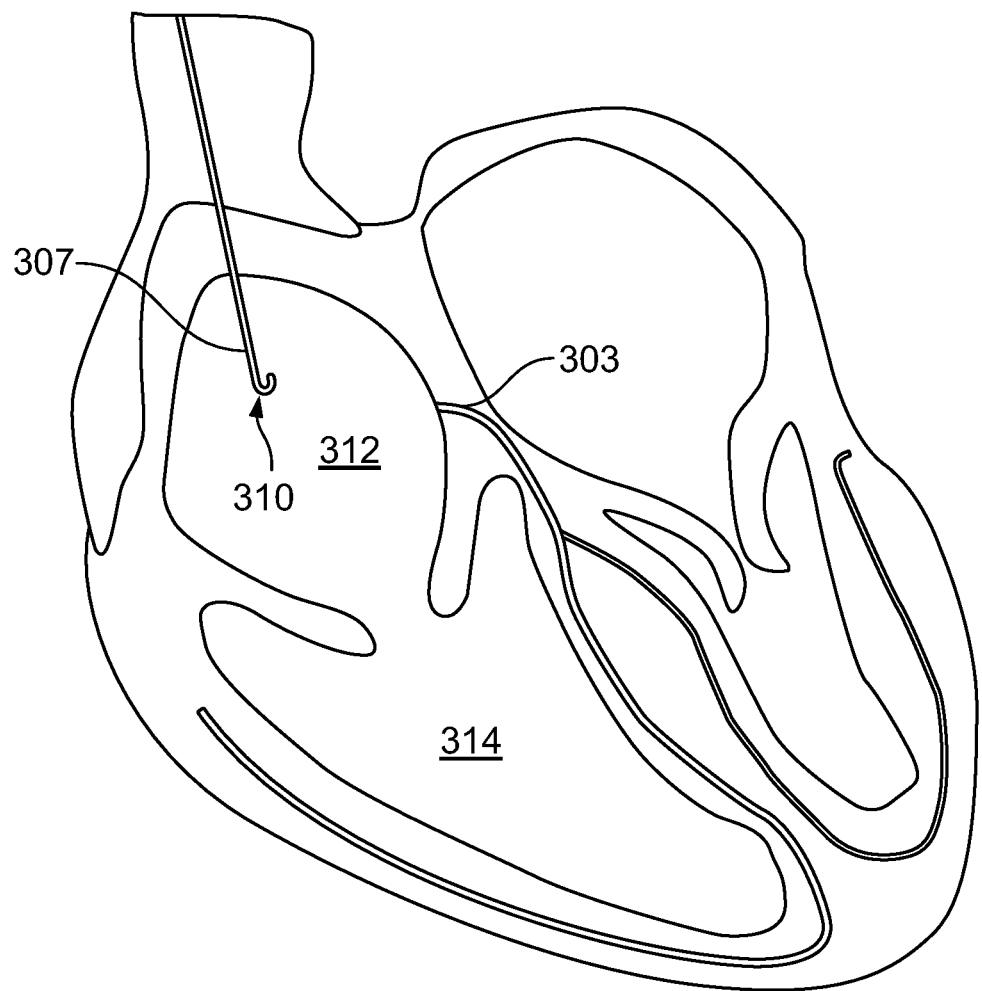
FIG. 7 is a schematic view of a heart having a guidewire advanced therein in accordance with the method of FIG. 6.

As shown in FIG. 5A, the handle 204 may include a hemostasis hub 212 for accepting and coupling to (e.g., tethering to) a proximal end of the catheter 202. The catheter 202 has a catheter lumen 282 (FIG. 5B) that is sized to receive a guidewire, such as the guidewires 305 (FIG. 9A), 307 (FIG. 7). The hemostasis hub 212 includes an entrance that permits access to the catheter lumen 282. The fluid flushing assembly 208 is also configured to mechanically couple to the hemostasis hub 212 and fluidly couple to the catheter lumen 280 through the hemostasis hub 212.

The catheter 202 is configured to introduce a guidewire and/or lead into a designated anatomical region (e.g., a patient's heart). Optionally, the catheter 202 may be steerable so that an end of the distal end segment 224 may be located proximate to and face the target SOI. To this end, the catheter 202 may include a plurality of sheath segments or portions. For example, the catheter 202 may include a proximal segment 221, a body segment 222, a deflectable segment 223, and the distal end segment 224. Based on its intended use, the catheter 202 may be configured to exhibit various properties. For example, the catheter may be maneuverable and have a sufficient columnar strength for being inserted through a tortuous vascular system. The catheter may also have sufficient kink-resistance so as to bend smoothly. Multiple layers of the catheter may be configured to have these and other properties.

The delivery system 200 may also include an obturator/dilator 220. In FIG. 5A, a proximal end 292 of the obturator/dilator 220 is shown and a distal end 225 of the obturator/dilator 220 is also shown. The distal end 225 may be wedge-shaped or cone-shaped (e.g., conical). As discussed below, the obturator/dilator 220 is configured to enlarge an opening for access to the vascular system and/or to provide support for the catheter 202 as the catheter 202 is being maneuvered.

Figure 5C:
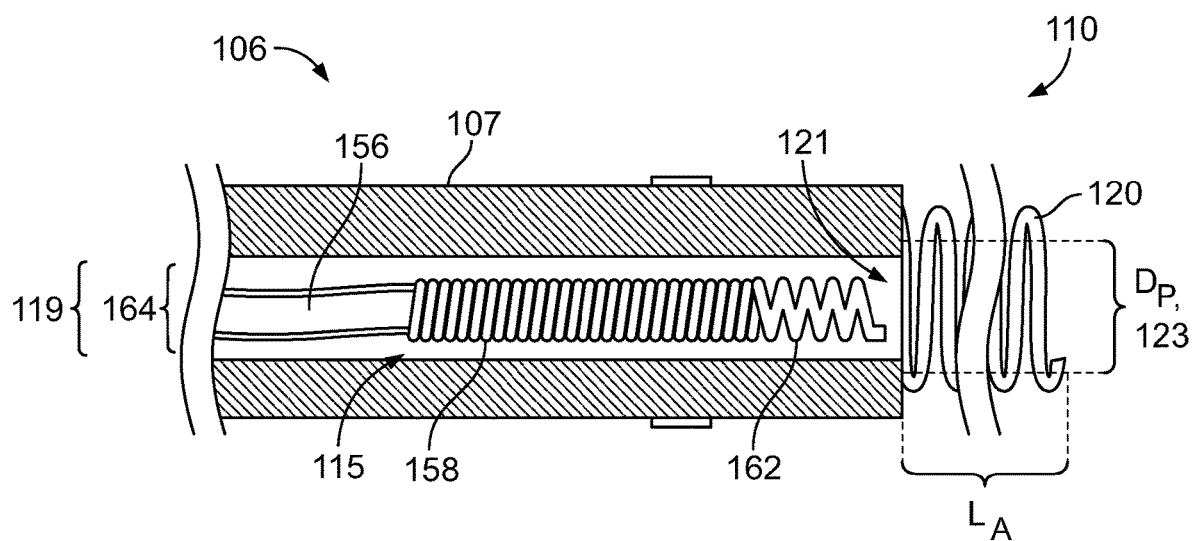
FIG. 5C is an enlarged cross-sectional view of a distal end of the implantable lead of FIG. 3 showing the active guidewire of FIG. 4 disposed within a lumen of the implantable lead.

FIG. 5C is an enlarged cross-sectional view of the distal end 110 of the implantable lead 106. The lumen 115 of the implantable lead 106 may have a diameter 119 that is sized to allow the active guidewire 150 to pass therethrough. For example, the lumen 115 of the implantable lead 106 may have a proximal opening (not shown) and a distal opening 121 that are sized relative to the active guidewire 150 so that the active guidewire 150 may move through each of the openings. For example, the distal opening 121 may be sized to allow the fixation anchor 162 and at least a portion of the coil 158 to pass therethrough.

The tip electrode 120 may constitute a fixation anchor that is configured to fixate with tissue at the target SOI. The tip electrode 120 may also be sized relative to the active guidewire 150. For example, the tip electrode 120 may define an anchor passage 123 that is aligned with the lumen 115 of the lead body 107. The anchor passage 123 may have a diameter DP that is sized to permit the tip electrode 120 to slide over the active guidewire 150 (or vice versa) as the active guidewire 150 slides through the lumen 115. More specifically, the anchor passage 123 and the wire body 156 are configured so that the implantable lead 106 may be inserted over the proximal end (not shown) of the active guidewire 150 and advanced along the active guidewire 150 toward the target SOI. Likewise, the fixation anchor 162 of the active guidewire 150 and the anchor passage 123 of the tip electrode 120 are configured so that the fixation anchor 162 may pass through the anchor passage 123 as the active guidewire 150 is withdrawn from the target SOI. For example, the diameter DP may be between 0.025" and 0.045" or, more particularly, between 0.030" and 0.040".

Also shown in FIG. 5C, the tip electrode 120 has a length LA. The length LA may be increased or decreased based on the target SOI. For example, the length LA may be increased to reach His bundles or bundle branches that are greater than 2.0 millimeters below the endocardial surface. In such embodiments, a proximal end of the tip electrode 120 (e.g., end that is closer to the lead body) may be coated with an insulating material, such as parylene, to maintain the impedance of the tip electrode within a desired range for pacing electrodes. Likewise, the tip electrode 120 may be configured based upon the tissue near the target SOI to ensure that the tip electrode 120 may reach a desired region within the target SOI. For example, the diameter of the wire that defines the tip electrode 120 may be increased or may have a material selected for its particular application.

Figure 6:
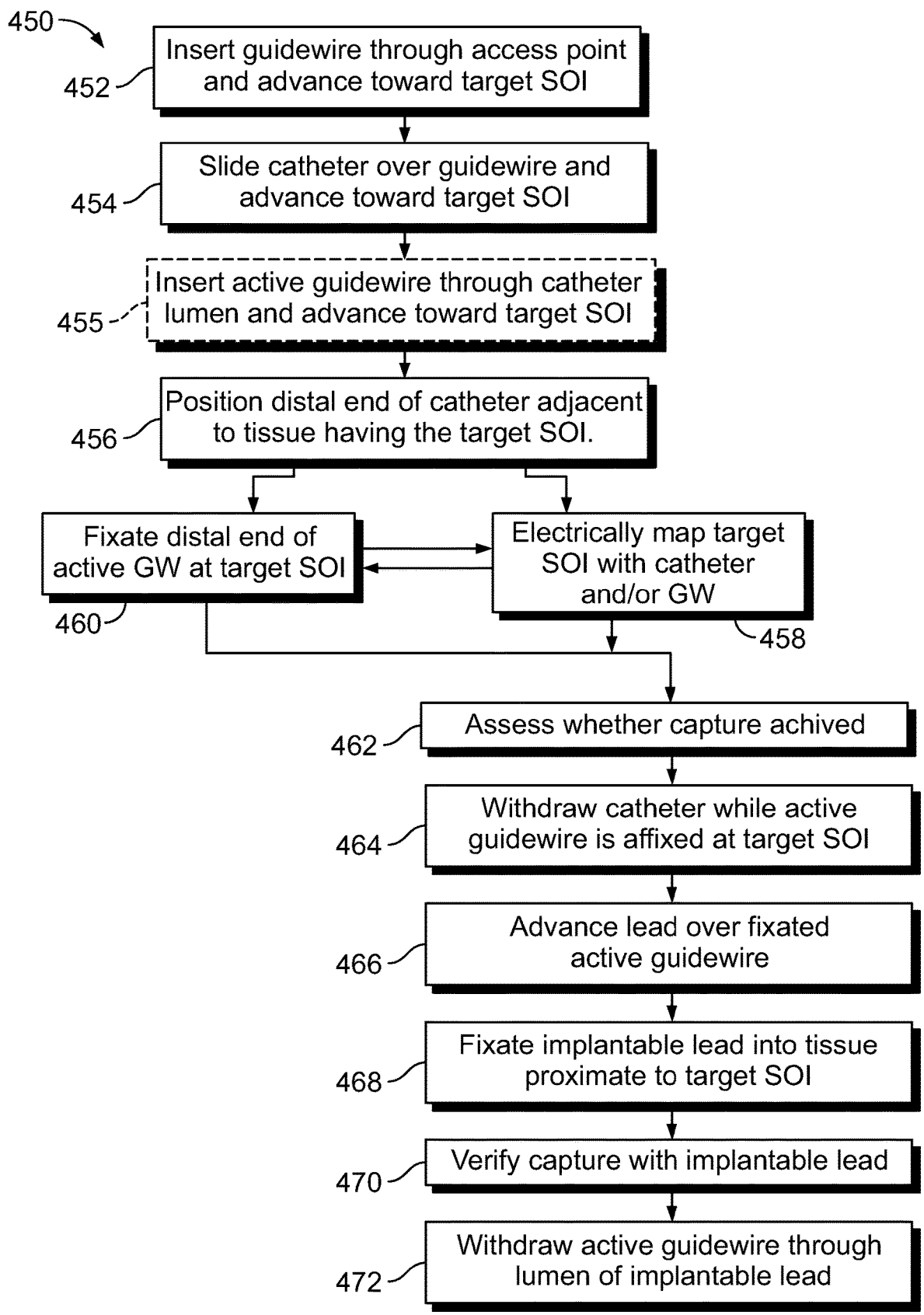
FIG. 6 is a block diagram of a method of implanting a medical device in accordance with an embodiment that uses the active guidewire of FIG. 5.

FIG. 6 is a flowchart illustrating a method 450 of positioning an implantable lead with respect to cardiac tissue. The method 450 is described with reference to FIGS. 7-14. The method 450 is illustrated in the context of HBP but may be suitable for other procedures. Particular embodiments utilize an electrically-active mapping guidewire with active fixation for use with a HIS-bundle implantation catheter. The systems and methods may promote normal conduction through the HIS-Purkinje system. Pacing at the bundle of His may prevent the negative effects of RV pacing and promote ventricular synchrony.

With reference to FIG. 7, a guidewire 307 is inserted through an access point of the vascular system. In some embodiments, the guidewire 307 is a catheter-positioning guidewire that is intended to be removed after a catheter is positioned within a designated space of the vascular system but prior to the lead being affixed to tissue. As such, the guidewire 307 may not be an active guidewire. In other embodiments, however, the guidewire 307 may be an active guidewire that may be used to position the catheter within the designated space and also to identify a location of a target SOI 303.

The guidewire 307 has a distal segment 310. Optionally, the distal segment 310 may have a predetermined shape to aid positioning of the guidewire 307. For example, the distal segment 310 may provide a J-shaped distal end or tip of the guidewire 307. As the guidewire 307 is navigated through the vascular system, the curved distal segment 310 may reduce the likelihood of the guidewire 307 inadvertently snagging or engaging other tissue.

The access point may be created by a needle (not shown) that is inserted through an incision of the body and into the vascular system. This process may be similar to the Seldinger technique. For example, a venous needle stick may be inserted through the subclavian vein or another vein, thereby creating an access point. After identifying the vein, the guidewire 307 may be inserted, at 425 (FIG. 6), through the access point and into the vascular system. The guidewire 307 is directed into a predetermined region of the vascular system having a target SOI 303.

The guidewire 307 and the distal segment 310 in particular may be guided and positioned within the chamber using medical imaging. For example, the guidewire 307 may be tracked using fluoroscopy. As shown in FIG. 7, the distal segment 310 may be directed into a chamber of the heart having the target SOI 303. In FIG. 7, the chamber is the right atrium 312. In other embodiments, however, the chamber may be the right ventricle 314.

Figure 8A:
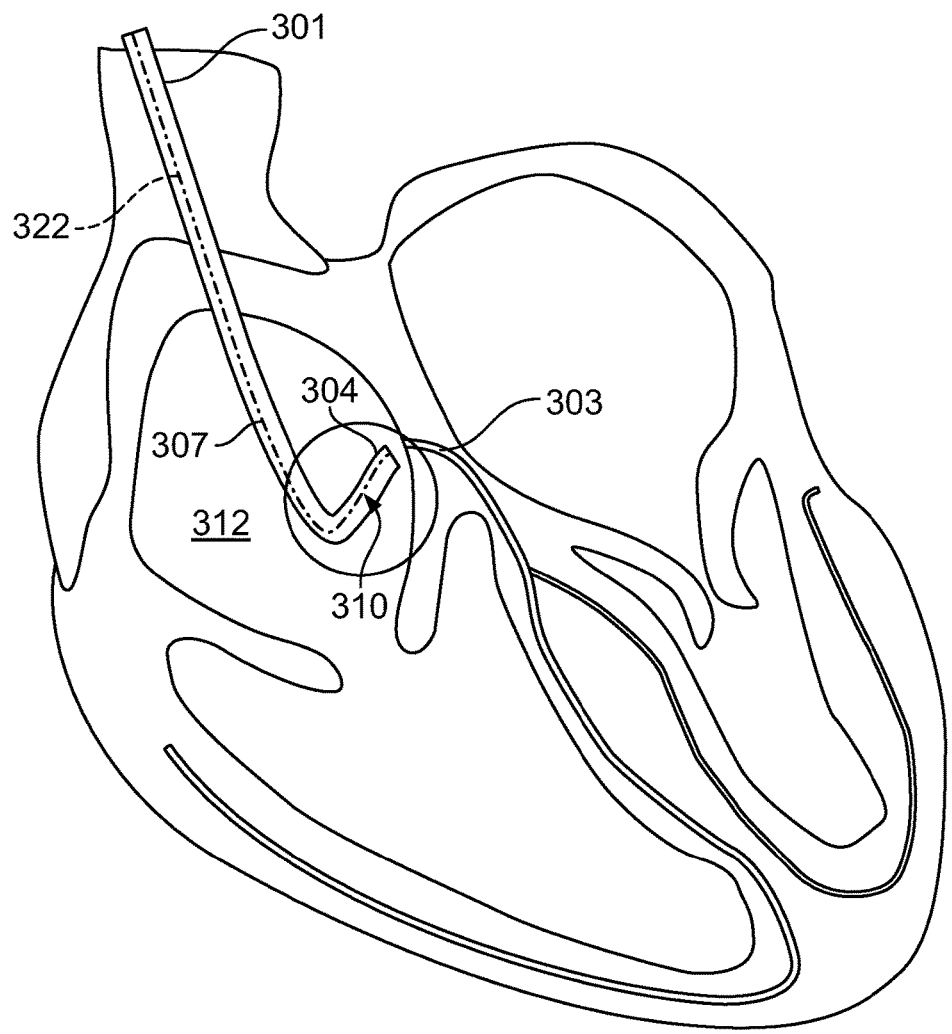
FIG. 8A illustrates the schematic view of the heart after a catheter has been advanced over the guidewire into the right atrium of the heart.
Figure 8B:
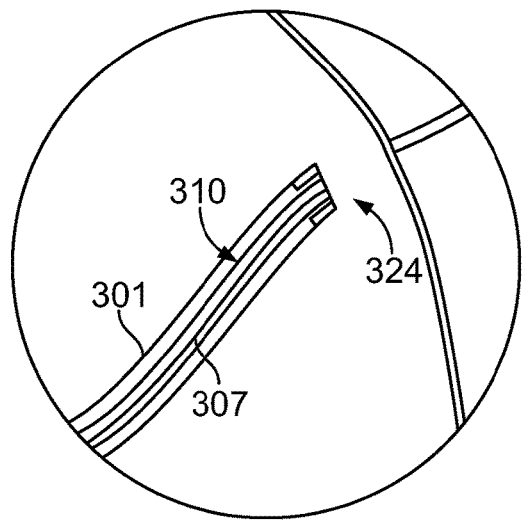
FIG. 8B illustrates an enlarged view of a distal end of the catheter shown in FIG. 8A after the catheter slides over the guidewire.

Turning to FIGS. 8A and 8B, with the distal segment 310 positioned within the designated chamber, a catheter 301 can be inserted through the access point. The catheter 301 is advanced, at 454 (FIG. 6), along the guidewire 307. The catheter 301 may include features that are similar or identical to the catheter 202 (FIG. 5A) and may be controlled by a delivery system, such as the delivery system 200 (FIG. 5A).

Optionally, the catheter 301 may include an obturator/dilator 220 within a lumen 322 of the catheter 301. The obturator/dilator 220 may also include a passage (not shown) through which the guidewire 307 may extend. The obturator/dilator 220 can have a wedge-shaped or cone-shaped distal end 225 that aids in enlarging the access point. When initially inserted through the access point, the catheter 301 may have a substantially straight configuration and may include the obturator/dilator 220 positioned at or near the distal end of the catheter 301 to enlarge the access point and to provide support for the catheter 301 as it is being maneuvered. The straight configuration of the catheter 301 may aid its passage through the superior vena cava and into the right atrium. Upon entry into the vein, the implanter may remove the obturator/dilator 220 and advance the catheter 301 over the guidewire 307 to the right atrium 312. Alternatively, the guidewire 307 may be removed before or after the obturator/dilator 220 is removed or along with removing the obturator/dilator 220.

Once a distal end 324 (FIG. 8B) of the catheter 301 has entered the right atrium 312, the catheter 301 may be further advanced toward the target SOI 303. For embodiments in which the guidewire 307 remains, the catheter 301 slides over the distal segment 310 and the distal segment 310 may be partially deflected. For example, the J-shaped distal segment 310 may partially straighten while also causing the catheter 301 to curve toward the target SOI 303. Alternatively, the distal end 324 of the catheter 301 may be steered within the right atrium 312 by the implanter without assistance from the guidewire 307.

Figure 9A:
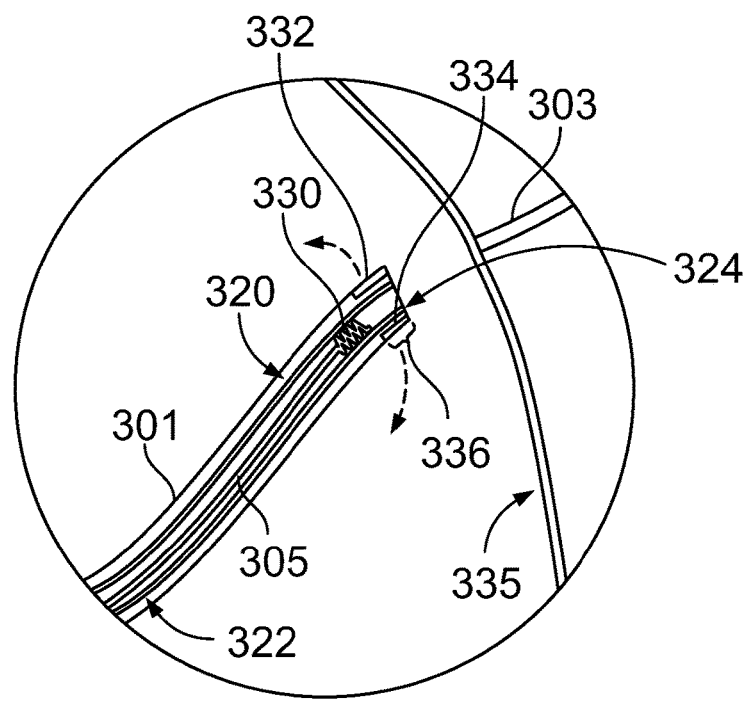
FIG. 9A illustrates an enlarged view of the heart after an active guidewire is inserted through a lumen of the catheter.
Figure 9B:
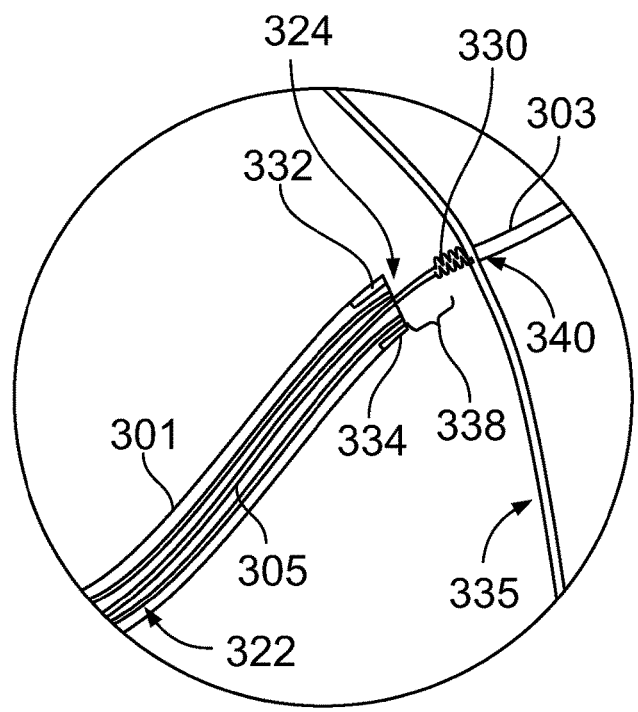
FIG. 9B illustrates an enlarged view of the heart after a distal segment of the active guidewire clears a distal end of the catheter and approaches a target site-of-interest (SOI).

For embodiments in which the catheter-positioning guidewire 307 is used, the method 450 (FIG. 6) may also include replacing the catheter-positioning guidewire 307 with an active guidewire 305 (shown in FIG. 9B). After removing the catheter-positioning guidewire 307, an active guidewire 305 may then be inserted, at 455, through the lumen 322 and advanced toward the target SOI 303 as guided by the catheter 301. At 456 (FIG. 6), the distal end 324 of the catheter 301 may be positioned adjacent to tissue having the target SOI 303. Although FIG. 6 indicates that the catheter 301 is positioned adjacent to the tissue after inserting the active guidewire 305, it should be understood that the catheter 301 may be positioned prior to the active guidewire 305 being inserted or as the active guidewire 305 is inserted.

FIG. 9A shows a distal end 320 of the active guidewire 305 disposed within the lumen 322 of the catheter 301. The distal end 320 includes a fixation anchor 330. In FIG. 9A, the active guidewire 305 is in a retracted position such that a tip of the fixation anchor 330 is located within the lumen 322 and the catheter 301 surrounds the entirety of the fixation anchor 330. In the retracted position, the fixation anchor 330 may not be aligned with or not co-located with electrodes 332, 334 of the catheter 301. For example, the fixation anchor 330 may be positioned at a depth 336 that is measured between a tip of the fixation anchor 330 and a tip of the distal end 324 of the catheter 301 (or an end of the lumen 322). The depth 336 may be configured such that electrodes 332, 334 of the catheter 301 are positioned closer to the target Sal 303 and such that the conductive material of the fixation anchor 330 does not interfere with the electrodes 332, 334 ability to detect electrical signals and/or supply electrical current.

FIG. 9B shows the distal end 320 of the active guidewire 305 in a projected (or protracted) position. In the projected position, the fixation anchor 330 may be pressed against a surface of the target SOI 303. In FIG. 9B, the surface is the endocardial surface of the right atrium. The fixation anchor 330 may be positioned at a clearance (or a separation distance) 338 that is measured between the fixation anchor 330 and the tip of the distal end 324 of the catheter 301. The clearance 338 may be configured such that the fixation anchor 330 is positioned in front of the electrodes 332, 334 and closer to the target SOI 303. The clearance 338 may be configured to improve detection of electrical signals from the target SOI during a mapping operation. For example, the clearance 338 may be configured to improve sensing between the active guidewire fixation anchor electrode 330 and 332 and/or 334 electrodes.

Figure 9C:
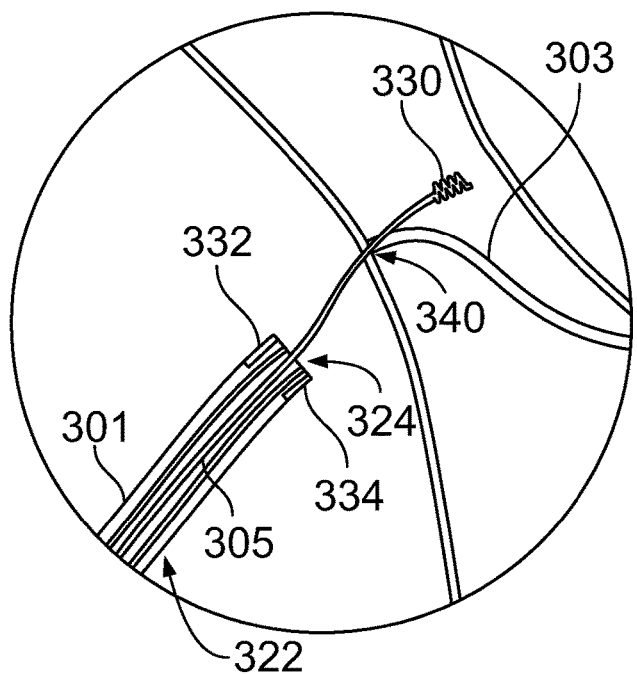
FIG. 9C illustrates an enlarged view of the heart after the active guidewire has been fixated to the target SOI.

FIG. 9C shows the distal end 320 of the active guidewire 305 fixated to tissue of the target SOI 303. To secure the fixation anchor 330, the implanter may rotate the active guidewire 305 while pressing the fixation anchor 330 into the surface. The fixation anchor 330 may pierce the tissue and forces provided by rotating the fixation anchor 330 and pressing the fixation anchor 330 forward may drive the fixation anchor 330 into the tissue.

At any of the configurations and spatial relationships shown in FIGS. 9A, 9B, and 9C, the target SOI 303 may be electrically mapped to identify a more precise location for implanting a lead. In particular embodiments, the target SOI 303 includes the His bundle. For most individuals, the His bundle is located within a membranous portion of the interventricular septum. A portion of the proximal bundle may exist within a right atrial portion of the septum superior to the tricuspid valve annulus. At this location, the His bundle may be surrounded by fibrous connective tissue. Within the right ventricular portion of the septum, the His bundle divides to form the right and left bundles.

The target SOI may be electrically mapped, at 258, by (a) the catheter 301 alone, (b) a combination of the catheter 301 and the active guidewire 305, or (c) the active guidewire 305 only. Optionally, the mapping process may include detecting signals from only two of (a), (b), or (c) or include detecting signals from each of (a), (b), or (c). In some embodiments, the mapping process may only include detecting signals from either (b) or (c) or from each of (b) and (c). For example, under control of one or more processors configured with specific executable instructions, an external programmer device may deliver stimulation energy through at least one of the catheter or the active guide wire to the target SOI. Alternatively or in addition to delivering stimulation energy, the external programmer device may sense an evoked response at the target SOI from at least one of the catheter or the active guidewire.

Returning to FIG. 9A, the distal end 324 of the catheter 301 may be steered toward the target SOI. In some embodiments, the target SOI 303 may be initially mapped (or approximately located) using the electrodes 332, 334 of the catheter 301. Sensing between 332 and 334 provides a small dipole that allows for precisely targeting a site proximate the His or bundle branch, the SOI 330. The implanter may operate a delivery system, such as the delivery system 200 (FIG. 5A), to position the distal end 324 of the catheter 301. Deflecting the catheter 301 may be accomplished by an actuator (e.g., actuator 235 shown in FIG. 5A) that is operably coupled to segments (e.g., segments 221-223 shown in FIG. 5A). With a proximal segment of the catheter 301 positioned in the superior vena cava, the actuator may move a deflectable segment of the catheter 301 such that a distal end 324 of the catheter 301 will point generally toward a wall surface 335. The wall surface 335 may be, for example, the surface of an atrial wall proximate to where the target SOI is believed to be located. The distal end 324 may be in close proximity to the septum, such as within 15 millimeters or less.

An external programmer device may be configured to be electrically coupled to a proximal end of the catheter 301. The catheter 301 may communicate electrical signals between the external programmer device and the electrodes 332, 334 for electrically mapping the target SOI 303. For example, the electrodes 332, 334 may sense electrical signals and communicate these electrical signals to the external programmer device for electrically mapping the target SOI 303. In such instances, it may be desirable to position the fixation anchor 330 at least the depth 336 within the lumen 322. If electrical signals are received from the electrodes 332 and 334, the implanter may know that the distal end 324 of the catheter 301 is at least approximately aligned with the target SOI 303.

If the electrodes 332, 334 are not receiving electrical signals, or if the signals are very faint, the implanter may maneuver the distal end 324 of the catheter 301 by small movements of the actuator (e.g., in either a forward or reverse direction) to scan the atrial wall as indicated by the dashed arrows in FIG. 9A. The small movements of the actuator will deflect the deflectable section of the catheter 301 by small amounts. A surface point 340 (shown in FIG. 9B) may be identified when the signals received by the electrodes 332, 334 are strongest.

Alternatively or in addition to using the catheter 301, the surface point 340 may be identified using the fixation anchor 330 of the active guidewire 305. More specifically, the fixation anchor 330 may be pressed against a series of points along the wall surface 335. When against the wall surface 335, the active guidewire 307 may at least one of deliver stimulation energy or detect an evoked response.

The point having the strongest signal may be designated as the surface point 340 through which the fixation anchor 330 will be submerged. Optionally, the electrical mapping may occur in unipolar mode by sensing between the fixation anchor 330 and a remote electrode (not shown), such as a surgical clamp at the pocket. In other embodiments, the electrical mapping may occur by sensing between the fixation anchor 330 and at least one of the electrodes 332, 334. The external programmer device may be communicatively coupled to the active guidewire 305 so that the electrical programmer device may receive signals sensed by the active guidewire 305.

Accordingly, the surface point 340 may be generally located by mapping with the catheter 301 to identify a local region along the wall surface 335 and then more precisely located by measuring a series of points within this local region to identify the surface point 340. Alternatively, the surface point 340 may be identified by mapping only with the catheter 301. In such instances, the surface point 340 may be any point within the local region identified by the catheter 301. As yet another alternative embodiment, the surface point 340 is identified, without initially mapping, by measuring a series of points along the wall surface 335.

FIG. 9C shows the fixation anchor 330 after piercing through the surface point 340 and submerging within the tissue of the target SOI 303. With the surface point 340 identified, the method includes fixating, at 460 (FIG. 6), the distal end 324 of the active guidewire 305 to the target SOI 303. More specifically, the fixation anchor 330 may be pressed against the wall surface 335 as the active guidewire 305 is rotated. In addition to urging the fixation anchor 330 into the tissue, the rotational force provided to the fixation anchor 330 by the implanter further drives the active guidewire 305 into the tissue. At 462 (FIG. 6), additional measurements may be acquired to assess whether capture of the target SOI 303 has been achieved. These measurements may be acquired at different depths within the tissue.

Figure 9D:
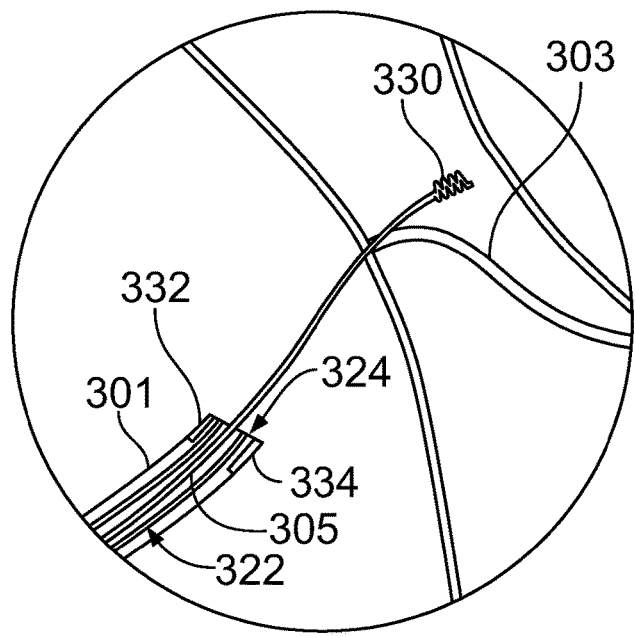
FIG. 9D illustrates an enlarged view of the heart as the catheter is withdrawn along the active guidewire while the distal end of the active guidewire remains fixated to the target SOI.

At 464 (FIG. 6), the catheter 301 may be withdrawn. As shown in FIG. 9D, the active guidewire 305 may remain embedded within the tissue of the target SOI 303. At 466 (FIG. 6), an implantable lead 456 (FIG. 9E) may be advanced over the active guidewire 305. More specifically, a proximal end of the active guidewire 305 may inserted into a lumen 365 (FIG. 9E) of the implantable lead 356. The implantable lead 356 may be inserted through the access point and urged toward the target SOI while tracking along the active guidewire 305.

Figure 9E:
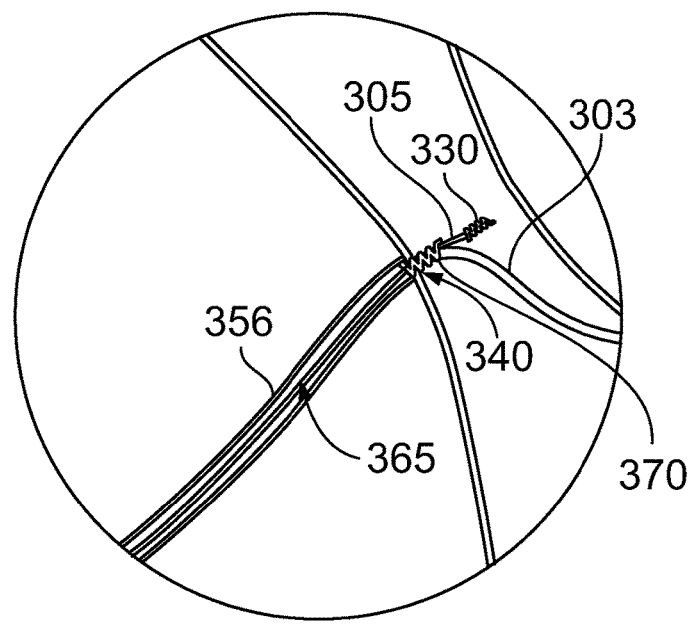
FIG. 9E illustrates an enlarged view of the heart after the lead has been advanced toward the target SOI along the active guidewire and after a lead anchor has been fixated to the target SOI.

FIG. 9E shows a lead anchor 370 of the implantable lead 356 fixated to the tissue of the target SOI. With the fixation anchor 330 of the active guidewire 305 remaining secured to the target SOI, a lead anchor 370 of the implantable lead 356 is guided to the surface point 340. At 468 (FIG. 6), the lead anchor 370 may be fixated to the tissue that is proximate the target SOI 303. Similar to the fixation anchor 330, the lead anchor 370 may be pressed against the wall surface 335 as the implantable lead 305 is rotated. In addition to urging the lead anchor 370 into the tissue, the rotational force provided to the lead anchor 370 by the implanter drives the lead anchor 370 into the tissue.

Figure 9F:
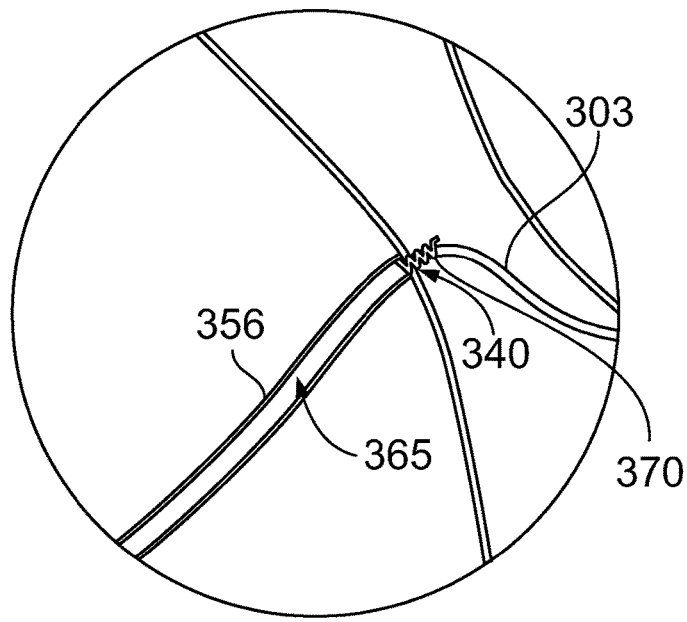
FIG. 9F illustrates an enlarged view of the heart showing the lead in an operating position after the active guidewire has been withdrawn through a lumen of the lead.

FIG. 9F shows the implantable lead 356 in an operating position with the lead anchor 370 functioning as a tip electrode of the implantable lead 356. At 470, the lead anchor 370 may sense electrical activity from the target SOI 303 to verify capture of the target SOI 303. The fixation anchor 330 may also be used at this time to verify capture. In FIG. 9F, the target SOI is the His bundle.

At 472, the active guidewire 305 may be withdrawn. For example, the implanter may gently pull the active guidewire 305 while also rotating the active guidewire 305 in an opposition direction. As described with respect to FIG. 5C, the active guidewire 305 may be removed through an anchor passage (not shown) of the lead anchor 370.

Figure 10A:
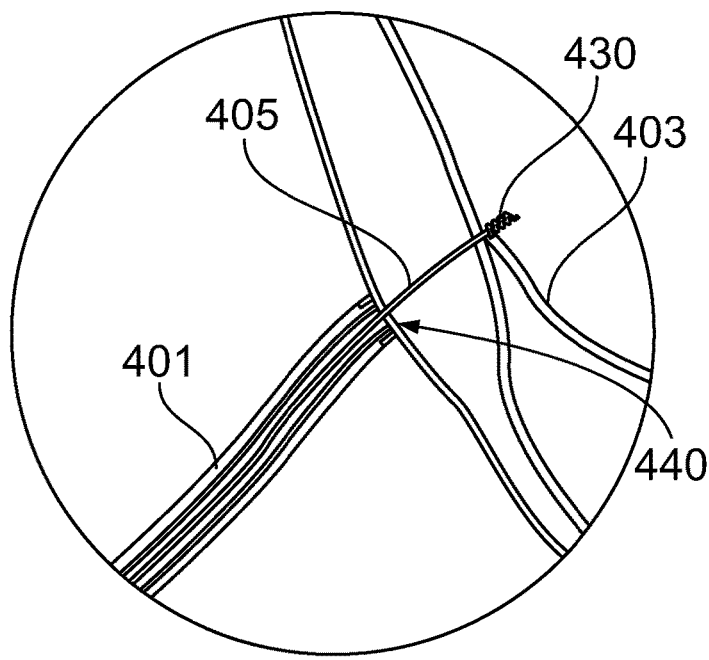
FIG. 10A is an enlarged view of a heart after a distal segment of an active guidewire, in accordance with an embodiment, clears a distal end of a catheter and has been fixated to a target SOI in a septa wall of the left ventricle.
Figure 10B:
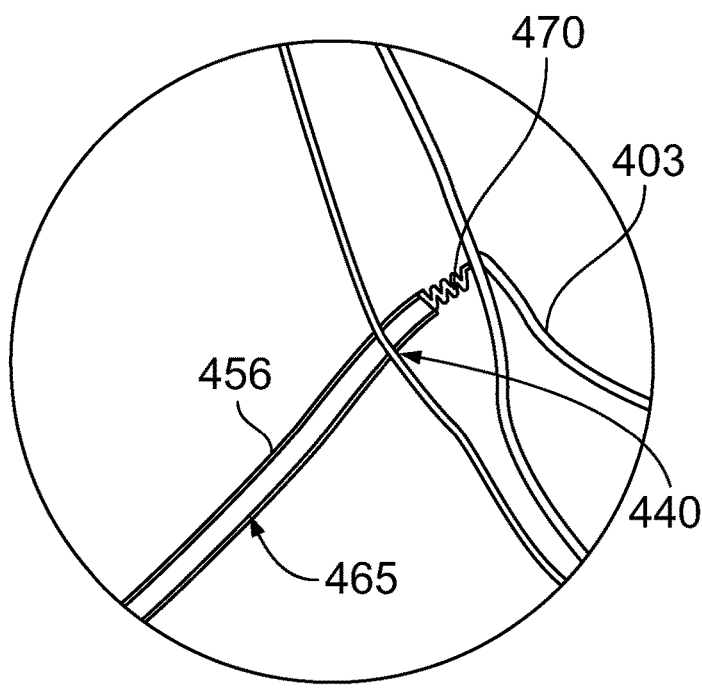
FIG. 10B is an enlarged view of the heart illustrating a lead in an operating position after the active guidewire has been withdrawn through a lumen of the lead.

FIGS. 10A and 10B illustrate another embodiment of the method 450 (FIG. 6) in which a target SOI 403 is one of the bundle branches located in the septum wall between the right and left ventricles. As shown in FIG. 10A, a fixation anchor 430 of an active guidewire 405 is capable of driving greater depths into the septum wall. In such instances, a catheter 401 may provide additional support to the active guidewire 405. For example, the active guidewire 405 at the surface point 440 may be held straight by the catheter 401 so that the force applied by the implanter does not cause the active guidewire 405 to bend or kink. For embodiments in which the target SOI 403 has greater depths, such as the depths where bundle branches may be located, the implantable lead 456 may be driven to greater depths using lead anchors 470 have greater lengths. As described herein, such lead anchors may be coated with an insulating material to control impedance.

Figure 11A:
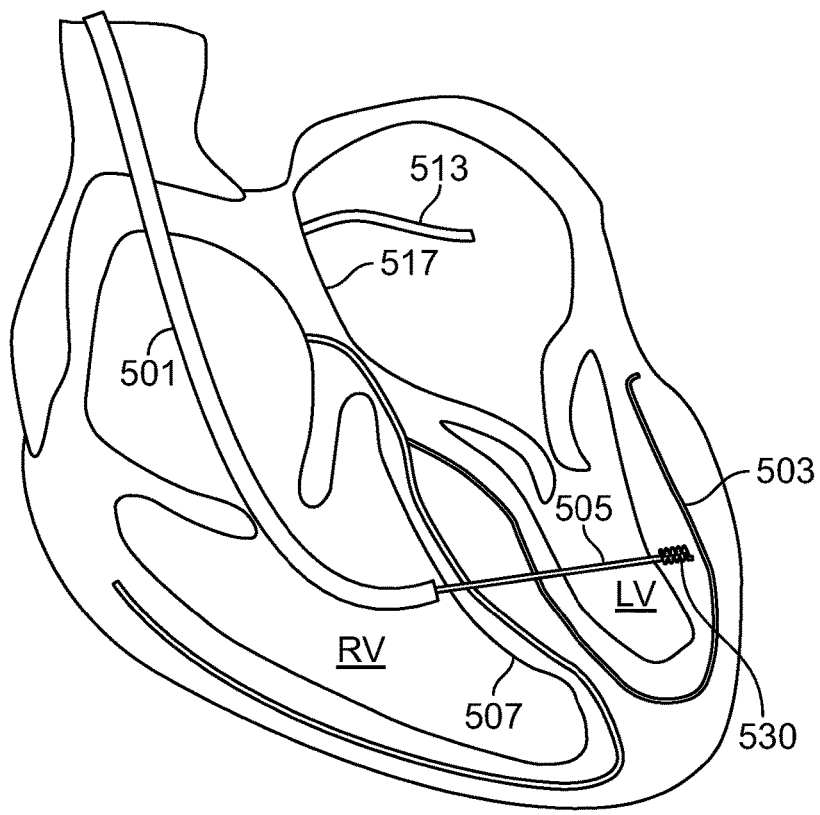
FIG. 11A illustrates a schematic view of the heart after a distal end of an active guidewire, in accordance with an embodiment, has advanced through a septa wall separating the right and left ventricles and submerged into a wall of the left ventricle proximate to a target SOI.
Figure 11B:
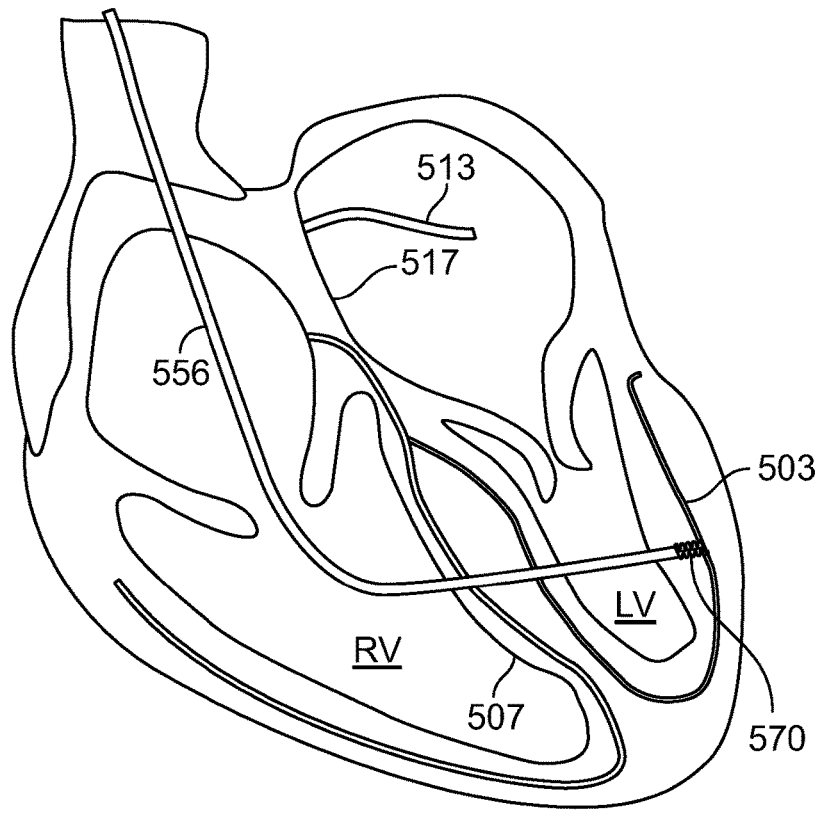
FIG. 11B illustrates a schematic view of the heart after a distal end of a lead, guided by the active guidewire of FIG. 11A, has advanced through the septa wall and submerged into the wall of the left ventricle.

FIGS. 11A and 11B illustrate another embodiment of the method 450 (FIG. 6) in which a target SOI 503 is located on an opposite side of a septum wall 507. In such instances, the target SOI 503 is proximate the Purkinje fiber through the opposite left ventricle wall. In alternative embodiments, the target SOI is identified as 513 and is located on an opposite side of a septum wall 517 proximate to the Bachmann's bundle. The following is with reference to the septum wall 507 and the Purkinje fiber but may be similarly applied to the septum wall 517 and the Bachmann's bundle.

As shown in FIG. 11A, the active guidewire 505 may be driven through the septum wall 507, through the left ventricle, and into the septum wall that includes the Purkinje fiber. The active guidewire 505 may identify the target SOI 503 and whether it has been located as described above with respect to the target SOI 303. Accordingly, in some embodiments, the active guidewire 505 may be advanced through the right atrium and through the right ventricle. The distal end of the active guidewire 505 may be forced through the septa wall 507 separating the right and left ventricles, advanced through the left ventricle, and submerged into a wall of the left ventricle proximate the Purkinje fiber.

As shown in FIG. 11B, an implantable lead 556 may be advanced along the active guidewire 505, through the septum wall 507, and into the left ventricle. After the lead anchor 570 is submerged within the wall, the active guidewire 505 may be removed. In other embodiments, however, the catheter 501 may be removed and the active guidewire 505 may remain and function as a pacing lead. In such embodiments, the implantable lead 556 is not used.

Figure 12:
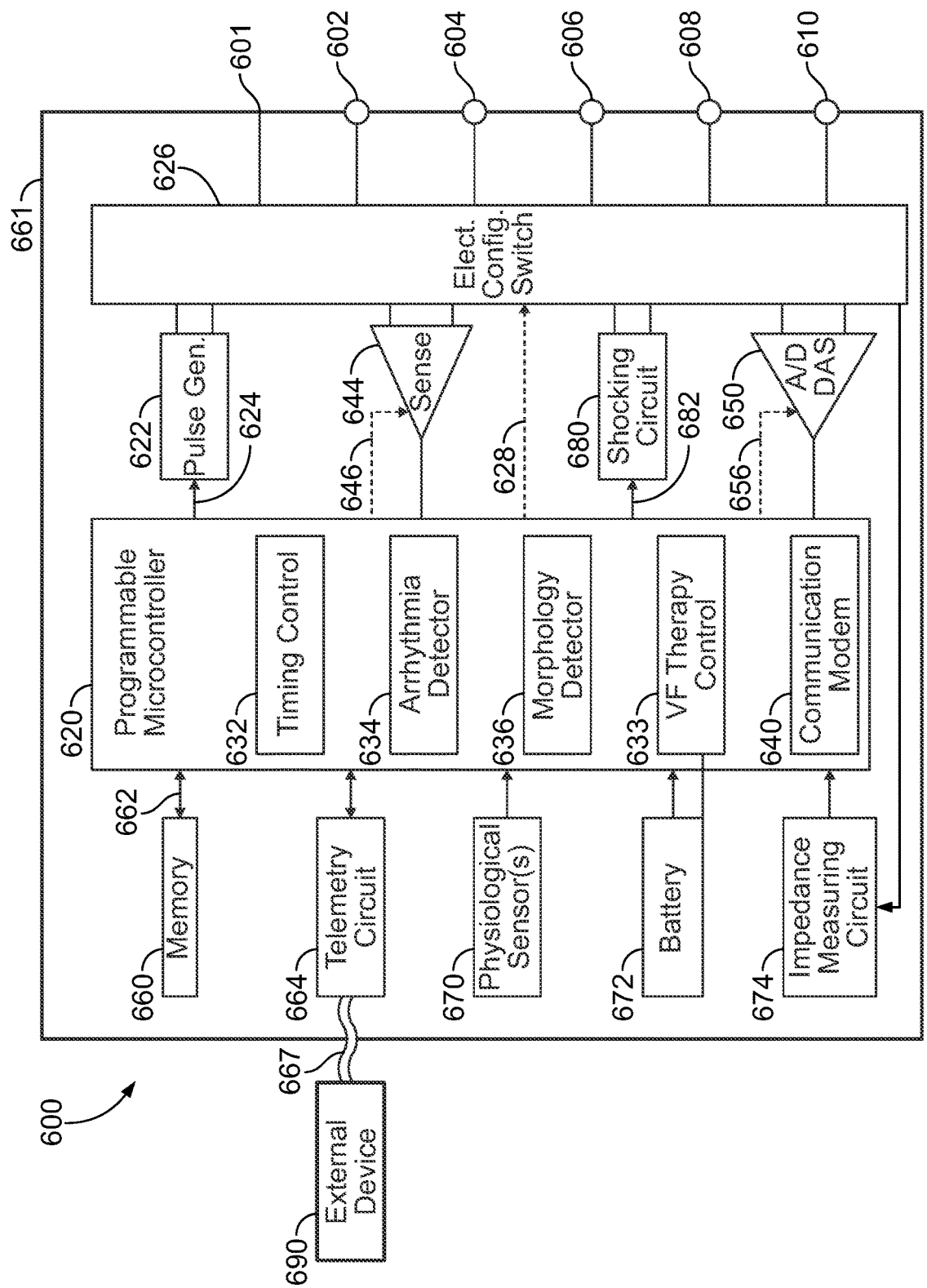
FIG. 12 illustrates a block diagram of an exemplary IMD that is configured to be implanted into the patient in accordance with one or more embodiments herein.

FIG. 12 illustrates a block diagram of an exemplary IMD that is configured to be implanted into the patient in accordance with embodiments herein. The IMD 600 may treat both fast and slow arrhythmias with stimulation therapy, including cardioversion, pacing stimulation, an implantable cardioverter defibrillator, suspend tachycardia detection, tachyarrhythmia therapy, and/or the like.

The IMD 600 has a housing 661 to hold the electronic/computing components. The housing 661 (which is often referred to as the "can," "case," "encasing," or "case electrode") may be programmably selected to act as the return electrode for certain stimulus modes. The housing 661 further includes a connector (not shown) with a plurality of terminals 601, 602, 604, 606, 608, and 610. The terminals may be connected to one or more leads that are located in various locations within and about the heart. Each lead may have one or more electrodes. The type and location of each electrode may vary. For example, the electrodes may include various combinations of ring, tip, coil, shocking electrodes, and the like.

The IMD 600 includes a programmable microcontroller 620 that controls various operations of the IMD 600, including cardiac monitoring and stimulation therapy. The microcontroller 620 includes a microprocessor (or equivalent control circuitry), one or more processors, RAM and/or ROM memory, logic and timing circuitry, state machine circuitry, and I/O circuitry. The IMD 600 further includes a pulse generator 622 that generates stimulation pulses for connecting the desired electrodes to the appropriate I/O circuits, thereby facilitating electrode programmability. The switch 626 is controlled by a control signal 628 from the microcontroller 620.

Optionally, the IMD 600 may include multiple pulse generators, similar to the pulse generator 622, where each pulse generator is coupled to one or more leads/electrodes and controlled by the microcontroller 620 to deliver select stimulus pulse(s) to the corresponding one or more electrodes. The IMD 600 includes sensing circuit 644 selectively coupled to one or more electrodes that perform sensing operations, through the switch 626 to detect the presence of cardiac activity in the chamber of the heart. The output of the sensing circuit 644 is connected to the microcontroller 620 which, in turn, triggers, or inhibits the pulse generator 622 in response to the absence or presence of cardiac activity. The sensing circuit 644 receives a control signal 646 from the microcontroller 620 for purposes of controlling the gain, threshold, polarization charge removal circuitry (not shown), and the timing of any blocking circuitry (not shown) coupled to the inputs of the sensing circuit 624.

In the example of FIG. 12, the sensing circuit 644 is illustrated. Optionally, the IMD 600 may include multiple sensing circuits 644, where each sensing circuit is coupled to one or more leads/electrodes and controlled by the microcontroller 620 to sense electrical activity detected at the corresponding one or more electrodes. The sensing circuit 624 may operate in, for example, a unipolar sensing configuration or a bipolar sensing configuration.

The IMD 600 further includes an analog-to-digital (A/D) data acquisition system (DAS) 650 coupled to one or more electrodes via the switch 626 to sample cardiac signals across any pair of desired electrodes. The A/D converter 650 is configured to acquire intracardiac electrogram signals, convert the raw analog data into digital data and store the digital data for later processing and/or telemetric transmission to an external device 690 (e.g., a programmer, local transceiver, or a diagnostic system analyzer). The A/D converter 650 is controlled by a control signal 656 from the microcontroller 620.

The microcontroller 620 is operably coupled to a memory 660 by a suitable data/address bus 662. The programmable operating parameters used by the microcontroller 620 are stored in the memory 660 and used to customize the operation of the IMD 600 to suit the needs of a particular patient. The operating parameters of the IMD 600 may be noninvasively programmed into the memory 660 through a telemetry circuit 664 in telemetric communication via communication link 667 (e.g., MICS, Bluetooth low energy, and/or the like) with the external device 690.

The IMD 600 can further include one or more physiological sensors 670. Such sensors are commonly referred to as "rate-responsive" sensors because they are typically used to adjust pacing stimulation rates according to the exercise state of the patient. However, the physiological sensor 670 may further be used to detect changes in cardiac output, changes in the physiological condition of the heart, or diurnal changes in activity (e.g., detecting sleep and wake states). Signals generated by the physiological sensors 670 are passed to the microcontroller 620 for analysis. While shown as being included within the IMD 600, the physiological sensor(s) 670 may be external to the IMD 600, yet still, be implanted within or carried by the patient. Examples of physiological sensors might include sensors that, for example, sense respiration rate, pH of blood, ventricular gradient, activity, position/posture, minute ventilation, and/or the like.

A battery 672 provides operating power to all of the components in the IMD 600. The battery 672 is capable of operating at low current drains for long periods of time, and is capable of providing a high-current pulses (for capacitor charging) when the patient requires a shock pulse (e.g., in excess of 2 A, at voltages above 2 V, for periods of 10 seconds or more). The battery 672 also desirably has a predictable discharge characteristic so that elective replacement time can be detected. As one example, the IMD 600 employs lithium/silver vanadium oxide batteries.

The IMD 600 further includes an impedance measuring circuit 674, which can be used for many things, including sensing respiration phase. The impedance measuring circuit 674 is coupled to the switch 626 so that any desired electrode and/or terminal may be used to measure impedance in connection with monitoring respiration phase. The IMD 600 is further equipped with a communication modem (modulator/demodulator) 640 to enable wireless communication with other devices, implanted devices and/or external devices. In one implementation, the communication modem 640 may use high frequency modulation of a signal transmitted between a pair of electrodes. As one example, the signals may be transmitted in a high frequency range of approximately 10-80 kHz, as such signals travel through the body tissue and fluids without stimulating the heart or being felt by the patient.

Optionally, the microcontroller 620 may control a shocking circuit 680 by way of a timing control 632. The shocking circuit 680 generates shocking pulses as controlled by the microcontroller 620. The shocking circuit 680 may be controlled by the microcontroller 620 by a control signal 682.

Although not shown, the microcontroller 620 may further include other dedicated circuitry and/or firmware/software components that assist in monitoring various conditions of the patient's heart and managing pacing therapies. The microcontroller 620 further includes a timing control 632, an arrhythmia detector 634, a morphology detector 636 and multi-phase therapy controller 633. The timing control 632 is used to control various timing parameters, such as stimulation pulses (e.g., pacing rate, atria-ventricular (AV) delay, atrial interconduction (A-A) delay, ventricular interconduction (V-V) delay, etc.) as well as to keep track of the timing of RR-intervals, refractory periods, blanking intervals, noise detection windows, evoked response windows, alert intervals, marker channel timing, and the like.

The morphology detector 636 is configured to review and analyze one or more features of the morphology of cardiac activity signals. For example, in accordance with embodiments herein, the morphology detector 636 may analyze the morphology of detected R waves, where such morphology is then utilized to determine whether to include or exclude one or more beats from further analysis. For example, the morphology detector 636 may be utilized to identify non-conducted ventricular events, such as ventricular fibrillation and the like.

The arrhythmia detector 634 may be configured to apply one or more arrhythmia detection algorithms for detecting arrhythmia conditions. By way of example, the arrhythmia detector 634 may apply various detection algorithms. The arrhythmia detector 634 may be configured to declare a ventricular fibrillation episode based on the cardiac events.

The therapy controller 633 is configured to perform the operations described herein. The therapy controller 633 is configured to identify a multi-phase therapy based on the ventricular fibrillation episode, the multi-phase therapy including a pacing therapy. The therapy controller 633 is configured to manage delivery of the burst pacing therapy at a pacing site in a coordinated manner after the one or more shocks. The pacing site may be located at a target SOI, such as a His Bundle. Optionally, other pacing sites may be located at one of a left ventricular (LV) site or a right ventricular (RV) site. The therapy controller 633 may configured to manage delivery of the shock along a shocking vector between shocking electrodes.

Reference throughout this specification to "one embodiment" or "an embodiment" (or the like) means that a particular feature, structure, or characteristic described in connection with the embodiment is included in at least one embodiment. Thus, appearances of the phrases "in one embodiment" or "in an embodiment" or the like in various places throughout this specification are not necessarily all referring to the same embodiment.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the inventive subject matter without departing from its scope. While the dimensions and types of materials described herein are intended to define the parameters of the inventive subject matter, they are by no means limiting and are exemplary embodiments. Many other embodiments will be apparent to one of ordinary skill in the art upon reviewing the above description. The scope of the inventive subject matter should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112(f) unless and until such claim limitations expressly use the phrase "means for" followed by a statement of function void of further structure.

What is claimed is:

1. A system for implanting a lead, comprising:
   an active guidewire having proximal and distal ends, the distal end configured to be located proximate to a target site of interest (SOI) within or proximate to a chamber of the heart, the distal end including a guidewire anchor configured to be attached to the target SOI:
an external programmer device configured to be connected to the active guide wire and to electrically map the target SOI by at least one of:
delivering a pacing pulse, as stimulation energy through the active guide wire, to the target SOI; or
sensing an evoked response at the target SOI from the guidewire; and
a lead having a lead body with proximal and distal ends and with a lumen extending along the lead body between the proximal and distal ends, the distal end of the lead body configured to receive the proximal end of the active guidewire, the lumen configured to permit the lead body to be advanced over the active guidewire until the distal end of the lead body is proximate the target SOI.

2. The system of claim 1, wherein the external programmer device is further configured to repeat at least one of the delivering or sensing operations multiple times to obtain additional measurements to electrically map the target SOI.

3. The system of claim 1, wherein the target SOI represents a HIS, the guidewire anchor configured to attach the distal end of the active guidewire into a wall of the heart proximate the HIS, the external programmer device configured to deliver a HIS paced event as the pacing pulse and to sense the evoked response to determine whether HIS capture was achieved based on the HIS paced event.

4. The system of claim 1, wherein the target SOI represents a left bundle branch, the guidewire anchor configured to attach the distal end of the active guidewire a predetermined depth into a septa wall separating the right and left ventricles, the external programmer device configured to deliver the pacing pulse through the distal end of the active guidewire to the left bundle branch.

5. The system of claim 1, wherein the target SOI represents a pacing site, wherein the external programmer device is configured to both deliver the pacing pulse, as the stimulation energy, through the guidewire to the target SOI and sense the evoked response at a sensing site within or proximate the heart separate from the pacing site.

6. The system of claim 1, wherein the target SOI represents a sensing site and wherein the external programmer device is configured to sense the evoked response at the sensing site following delivery of a pacing pulse at a pacing site within or proximate the heart separate from the sensing site.

7. The system of claim 1, further comprising:
a catheter configured to be advanced to or proximate the chamber of the heart having the target SOI, the catheter having a lumen with a size dimensioned to receive the active guidewire, the size of the lumen in the catheter being smaller than an outer dimension of the lead body, such that the lead does not fit through the lumen of the catheter.

8. The system of claim 7, wherein the catheter comprises at least one electrode positioned proximate to a distal end of the catheter, the at least one electrode configured to at least one of deliver stimulation energy to the target SOI or sense an evoked response at the target SOI.

9. The system of claim 1, wherein the lead includes a lead anchor coupled to the distal end of the lead body, the lead anchor defining an anchor passage that is aligned with the lumen of the lead body, the anchor passage sized to permit the lead anchor to slide over the active guidewire as the lumen is advanced over the active guidewire.

10. The system of claim 1, wherein the lead anchor includes a helical screw that wraps about the anchor passage.

11. A method of implanting a lead, the method comprising:
advancing an active guidewire to a target site of interest (SOI) within or proximate to a chamber of the heart;
electrically mapping the target SOI utilizing the active guidewire and an external programmer device by at least one of delivering a pacing pulse, as stimulation energy through the active guide wire, to the target SOI or sensing an evoked response at the target SOI from the guidewire;
fixating a distal end of the active guidewire at the target SOI; and
advancing a lead over the active guidewire until a distal end of the lead is located proximate the target SOI.

12. The method of claim 11, wherein the fixating the distal end of the active guidewire is performed before the electrically mapping the target SOI utilizing the active guidewire.

13. The method of claim 11, wherein the target SOI represents a HIS bundle region, the fixating the distal end includes attaching the distal end of the active guidewire into a wall of the heart proximate the HIS bundle region, and the electrically mapping includes delivering a HIS paced event as the pacing pulse, the method further comprising assessing whether capture of the HIS bundle region was achieved based on the HIS paced event.

14. The method of claim 11, wherein the target SOI represents a left bundle branch, wherein the fixating the distal end includes submerging the distal end of the active guidewire a predetermined depth into a septa wall separating the right and left ventricles, and wherein the electrically mapping includes delivering the pacing pulse through the distal end of the active guidewire to the left bundle branch.

15. The method of claim 11, wherein the target SOI represents a pacing site and wherein the electrical mapping includes both:
delivering the pacing pulse, as the stimulation energy, through the guidewire to the target SOI; and
sensing the evoked response at a sensing site within or proximate the heart separate from the pacing site.

16. The method of claim 11, wherein the target SOI represents a sensing site and wherein the electrical mapping includes sensing the evoked response at the sensing site following delivery of a pacing pulse at a pacing site within or proximate the heart separate from the sensing site.

17. The method of claim 11, further comprising prior to advancing the active guidewire:
advancing a J-tip guidewire, obturator, and catheter to or proximate the chamber of the heart having the target SOI;
withdrawing the obturator and J-tip guidewire;
inserting the active guidewire through the catheter to the target SOI; and
withdrawing the catheter before advancing the lead over the active guidewire.

18. The method of claim 11, wherein the advancing the active guidewire further comprises advancing the active guidewire through the right atrium and through the right ventricle, forcing the distal end of the active guidewire through a septa wall separating the right and left ventricles, advancing the distal end of the active guidewire through the left ventricle and submerging the distal end of the active guidewire into a wall of the left ventricle proximate the Purkinje fiber.

19. The method of claim 11, wherein the target SOI represents at least one of an atrial pacing site, a His bundle pacing site, a left bundle branch pacing site, a right bundle branch pacing site, and LV wall pacing site proximate the LV Purkinje fibers.

20. The method of claim 11, further comprising fixating a distal end of the lead to tissue at the target SOI and removing the guidewire by withdrawing the active guidewire along a lumen within the lead.

\* \* \* \* \*